US010156576B2

(12) United States Patent
Narimatsu et al.

(10) Patent No.: US 10,156,576 B2
(45) Date of Patent: Dec. 18, 2018

(54) METHOD FOR ENRICHMENT AND SEPARATION OF SPINAL FLUID GLYCOPROTEIN, METHOD FOR SEARCHING FOR MARKER FOR CENTRAL NERVOUS SYSTEM DISEASES WHICH UTILIZES THE AFOREMENTIONED METHOD, AND MARKER FOR CENTRAL NERVOUS SYSTEM DISEASES

(71) Applicant: National Institute of Advanced Industrial Science and Technology, Chiyoda-ku, Tokyo (JP)

(72) Inventors: Hisashi Narimatsu, Tsukuba (JP); Jun Hirabayashi, Tsukuba (JP); Atsushi Kuno, Tsukuba (JP); Hideki Matsuzaki, Tsukuba (JP); Yuzuru Ikehara, Tsukuba (JP); Hiromi Ito, Fukushima (JP); Yasuhiro Hashimoto, Fukushima (JP); Keiro Shirotani, Fukushima (JP); Satoshi Futakawa, Tokyo (JP); Hajime Arai, Tokyo (JP); Masakazu Miyajima, Tokyo (JP); Kazuo Fujihara, Sendai (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 15/071,419

(22) Filed: Mar. 16, 2016

(65) Prior Publication Data

US 2016/0187356 A1 Jun. 30, 2016

Related U.S. Application Data

(62) Division of application No. 13/994,435, filed as application No. PCT/JP2011/079218 on Dec. 16, 2011.

(30) Foreign Application Priority Data

Dec. 16, 2010 (JP) .................. 2010-280753

(51) Int. Cl.
 *G01N 33/68* (2006.01)
 *H01J 49/00* (2006.01)

(52) U.S. Cl.
 CPC ..... *G01N 33/6896* (2013.01); *G01N 33/6842* (2013.01); *H01J 49/0036* (2013.01); *G01N 2333/47* (2013.01); *G01N 2333/4728* (2013.01); *G01N 2400/40* (2013.01); *G01N 2800/285* (2013.01)

(58) Field of Classification Search
 CPC .......... G01N 33/6896; G01N 2333/47; G01N 2333/4728; G01N 2400/40; G01N 2800/28; G01N 33/6842; G01N 2800/285; H01J 49/0036

See application file for complete search history.

(56) References Cited

U.S. PATENT DOCUMENTS

2008/0220013 A1 9/2008 Hochstrasser et al.

FOREIGN PATENT DOCUMENTS

| JP | H11513372 A | 11/1999 |
|---|---|---|
| JP | 2008-184404 A | 8/2008 |
| JP | 2010-121980 A | 6/2010 |
| WO | 1997/011093 A2 | 3/1997 |
| WO | 02059604 A2 | 8/2002 |
| WO | 2010118035 A2 | 10/2010 |

OTHER PUBLICATIONS

Kanoh et al., (Biochemistry and Molecular Biology International 1997; vol. 43.No. 2, 1997).*
Chin et al (Arch Dis Child 2005;90:66-69).*
Hashimoto, Yasuhiro, et al., "Development of Method for Diagnosing Normal Pressure Hydrocephalus Using Glycoprotein Sugar Chain as Marker", Annual Report of the Research Committee of Normal Pressure Hydrocephalus Studies on the Epidemiology, Pathogenesis and Therapy, Supported by the Ministry of Health, Labor and Welfare of Japan (2008-Nanchi-General-017), Mar. 2010, pp. 23-24.
Ueda, Haruko et al., "Psathyrella Velutina Mushroom Lectin Exhibits High Affinity Toward Sialoglycoproteins Possessing Terminal N-Acetylneuraminic Acid α2,3-Linked to Penultimate Galactose Residues of Trisialy N-Glycans", Journal of Biological Chemistry, Jul. 12, 2002, vol. 277, No. 28, pp. 24916-24925.
International Search Report of the International Searching Authority, with English translation, dated Feb. 28, 2012, issued in connection with International Application No. PCT/JP2011/079218 (5 pages).
Ueda, Haruko, et al., "Interaction of a Lectin From Psathyrella Velutina Mushroom with N-acetylneuraminic Acid," FEBS Letters, 1999, vol. 448, No. 1, pp. 75-80.

(Continued)

Primary Examiner — Tracy Vivlemore
Assistant Examiner — Carmencita M Belei
(74) Attorney, Agent, or Firm — McCarter & English, LLP

(57) ABSTRACT

The purpose of the present invention is to develop: a method for selectively separating a glycoprotein derived from the central nervous system from a body fluid or a central nervous system cell; and a method for searching for an index marker for central nervous system diseases, which utilizes the aforementioned method. A protein derived from the central nervous system, which occurs in a trace amount in a body fluid or a central nervous system cell, can be selectively enriched by a two-stage separation procedure comprising removing a glycoprotein having sialic acid at a non-reducing terminal thereof from the body fluid or the central nervous system cell and then separating a glycoprotein having N-acetylglucosamine at a non-reducing terminal thereof.

9 Claims, 11 Drawing Sheets

Specification includes a Sequence Listing.

(56) References Cited

OTHER PUBLICATIONS

European Search Report based on co-pending European Application No. 11847931, dated May 11, 2015, 10 Pages.
European Search Report based on co-pending European Application No. 16173307, dated Sep. 23, 2016, 9 Pages.
Endo, Tamao, "Fractionation of Glycoprotein-Derived Oligonosaccharides by Affinity Chromatography Using Immobilized Lectin Columns", Journal of Chromatography A, 1996, vol. 720, pp. 251-261.
Feng, Shun, et al. "Enrichment of Glycoproteins Using Nanoscale Chelating Concanavalin A Monolithic Capillary Chromatography", Analytical Chemistry, 2009, vol. 81, pp. 3776-3783.
Hoffmann Andrea, et al., "Carbohydrate Structures of B-Trace Protein from Human Cerebrospinal Fluid: Evidence for "Brain Type" N-Glycosylation", Journal of Neurochemistry, 1994, vol. 63, Issue No. 6, pp. 2185-2196.
Lescuyer, Pierre, et al., "Prostaglandin D2 Synthase and Its Post-Translational Modifications in Neurological Disorders", Electrophoresis, 2005, vol. 26, pp. 4563-4570.
Taniguchi, Miyako, et al., "Sugar Chains of Cerebrospinal Fluid Transferrin as a New Biological Marker of Alzheimer's Disease", Dementia and Geriatric Cognitive Disorders, 2008, vol. 26, No. 2, pp. 117-122.
Sasso, et al., Biochemistry; 1999, vol. 64, Issue 7, pp. 839-844, Translation of Biokhimiya (Moscow).
Bowie, James U., et al., "Deciphering the Message in Protein Sequences: Tolerance to Amino Acid Substitutions", Science, Mar. 16, 1990, vol. 247, pp. 1306-1310.
Yerbury, Justin J., et al., "Extracellular Chaperones Modulate the Effects of Alzheimer's Patient Cerebrospinal Fluid on AB1-42 Toxicity and Uptake", Cell Stress and Chaperones, 2010, vol. 15, pp. 115-121.
Ottervald, Jan, et al., "Multiple Sclerosis: Identification and Clinical Evaluation of Novel CSF Biomarkers", Journal of Proteomics, Apr. 18, 2010, vol. 73, No. 6, pp. 1117-1132.

* cited by examiner

METHOD FOR ENRICHMENT AND SEPARATION OF SPINAL FLUID GLYCOPROTEIN, METHOD FOR SEARCHING FOR MARKER FOR CENTRAL NERVOUS SYSTEM DISEASES WHICH UTILIZES THE AFOREMENTIONED METHOD, AND MARKER FOR CENTRAL NERVOUS SYSTEM DISEASES

RELATED APPLICATIONS

This application is a divisional of U.S. application Ser. No. 13/994,435, filed Sep. 12, 2013, which is a national stage application filed under 35 U.S.C. 371 of International Application No. PCT/JP2011/079218 filed Dec. 16, 2011, which claims the benefit of Japanese Patent Application No. 2010-280753, filed Dec. 16, 2010, each of which is incorporated by reference herein in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119244_00090_Sequence_Listing. The size of the text file is 14 KB, and the text file was created on Feb. 24, 2016.

TECHNICAL FIELD

The present invention relates to a method for enriching and isolating a spinal fluid glycoprotein, a method for searching for a marker for central nervous system disease using the method, and a marker for central nervous system disease obtained by the search method.

BACKGROUND ART

Cerebrospinal fluid (spinal fluid) corresponds to extracellular fluid of the central nervous system (CNS) and is separated from blood components by the blood-brain barrier. The expression of central nervous system-derived proteins present mainly in this spinal fluid is likely to increase or decrease along with the onset of central nervous system disease. Accordingly, a central nervous system-derived protein whose expression level correlates with a particular central nervous system disease can serve as a promising diagnostic marker for the disease (Non Patent Literature 1).

Even the spinal fluid, however, is composed mainly of serum proteins (80% or more of its components) leaked into the brain fluid circulation system and actually contains central nervous system-derived proteins only in a trace amount (Non Patent Literature 1). In addition, heretofore known techniques are hardly capable of selectively isolating such central nervous system-derived proteins from the spinal fluid. Thus, the diagnostic marker cannot be searched for easily.

On the contrary, if central nervous system-derived proteins are leaked into blood, a low invasive and promising test method for central nervous system disease may be achieved by detecting the central nervous system-derived proteins in blood. Unfortunately, the amount of central nervous system-derived proteins in blood is much smaller than that of central nervous system-derived proteins in spinal fluid. Thus, the central nervous system-derived proteins in blood are more difficult to detect than those in spinal fluid.

Currently known diagnostic markers for central nervous system disease are, for example, trace substances such as tau protein or Aβ42 peptide, which is a causative factor of Alzheimer's disease (AD), and a cytokine for inflammatory disease (Non Patent Literature 2). Although the tau protein is an excellent diagnostic marker for AD, the expression of this protein means neuronal death. In this respect, the tau protein is insufficient for early diagnosis intended for the treatment of AD (avoidance of neuronal death). Also, the tau protein increases in other dementia types and thus, is not an AD-specific marker. Disadvantageously, the amount of the Aβ42 peptide varies only after progression of the disease. The cytokine permits sensitive assay but has the disadvantage of poor disease specificity.

In Patent Literature 1, the present inventor has found and disclosed a diagnostic drug for AD by focusing on the sugar chains of glycoproteins in serum. The serum glycoproteins, however, are mostly derived from the liver. In addition, their concentrations largely vary due to various diseases unrelated to AD. For example, so-called acute phase proteins such as C-reactive protein (CRP), mannose-binding protein, fibrinogen, haptoglobin, and α1-antitrypsin are known to largely vary in their amounts due to inflammation associated with mild infection, burn, and small scars, etc. Thus, the detection or enrichment of a central nervous system marker coexisting in a trace amount with serum proteins has encountered undesired technical difficulty.

In Patent Literature 2, the present inventors have hypothesized that the central nervous system contains a glycoprotein having a unique sugar chain structure, and screened for proteins differing in their sugar chain moieties between spinal fluid and serum using various antibodies. As a result, the present inventors have found that spinal fluid contains heretofore known transferrin-2 having α2,6 sialic acid (hereinafter, referred to as "Sia-α2,6-Gal" in the present specification, unless otherwise specified) at a non-reducing terminus, which is also found in large amounts in serum, as well as transferrin-1 having N-acetylglucosamine (hereinafter, referred to as "GlcNAc" in the present specification, unless otherwise specified) but no sialic acid residue at a non-reducing terminus. This transferrin-1 has been shown to be secreted from a spinal fluid-producing tissue choroid plexus. The present inventors have further revealed that this protein can serve as an index marker for idiopathic normal pressure hydrocephalus (iNPH), which is a spinal fluid metabolic disorder (Patent Literature 2). This result suggested that such a spinal fluid glycoprotein derived from the central nervous system has GlcNAc at a non-reducing terminus of the sugar chain but is free from Sia-α2,6-Gal.

PVL lectin is known as lectin strongly binding to non-reducing terminal GlcNAc. It has been the common general knowledge of the art that the PVL lectin hardly binds to non-reducing terminal Sia-α2,6-Gal (Non Patent Literature 3). Thus, those skilled in the art can predict that a spinal fluid glycoprotein having non-reducing terminal GlcNAc but no sialic acid residue, i.e., a spinal fluid glycoprotein derived from the central nervous system, can be enriched selectively by use of the PVL lectin. At the same time, those skilled in the art can predict that a terminal Sia-α2,6-Gal-containing glycoprotein, i.e., a serum glycoprotein can be removed selectively by use of the PVL lectin. Nonetheless, the present inventors have revealed that, unlike the common general knowledge of the art, in actuality, the PVL lectin also binds, albeit partially, to transferrin-2 having terminal Sia-α2,6-Gal. For example, as shown in FIG. 11, transferrin-2 (TF-2) is recovered in both a binding fraction BF (lane 4) and a nonbinding fraction NF (lane 5) of a PVL lectin column. This result indicates that a spinal fluid glycoprotein is difficult to selectively enrich using PVL lectin beads alone from a sample (body fluid such as spinal fluid or serum) containing a large amount of a glycoprotein having Sia-α2, 6-Gal at a non-reducing terminus of the sugar chain, such as a spinal fluid sample. Meanwhile, transferrin-2 exhibits strong affinity for SSA lectin and is recovered in a binding fraction BF (lane 2) of a SSA lectin column. Alternatively, central nervous system-derived spinal fluid transferrin-1 (TF-1) having only GlcNAc at a non-reducing terminus specifically binds to PVL lectin but do not bind to SSA lectin (lanes 7 to 10).

CITATION LIST

Patent Literature

Patent Literature 1: JP Patent No. 4385149; Patent Literature 2: JP Patent Publication (Kokai) No. 2010-121980 A (2010).

Non Patent Literature

Non Patent Literature 1: Korolainen M A. et al., 2010, J. Neurochem., 112 (6): 1386-1414; Non Patent Literature 2: Mattsson N et al., JAMA. 2009 Jul. 22; 302 (4); 385-93; Non Patent Literature 3: Ueda H. et al., 2002, J. Biol. Chem. 277 (28): 24916-24925.

SUMMARY OF INVENTION

Technical Problem

An object of the present invention is to develop a method for selectively isolating a central nervous system-derived glycoprotein from a body fluid such as spinal fluid, to develop a method for searching for an index marker for central nervous system disease based on the method, and to provide an index marker for central nervous system disease obtained using the search method.

Solution to Problem

In order to attain the object, the present inventors have also searched for central nervous system-derived glycoproteins other than transferrin-1 using PVL lectin in combination with various antibodies. As a result, the present inventors have revealed that a sugar chain having GlcNAc at its non-reducing terminus is also commonly found in many other spinal fluid glycoproteins derived from the central nervous system. This sugar chain structure is also found in serum glycoproteins. However, the serum glycoproteins have also been shown to contain sialic acid at another non-reducing terminus and structurally differ from the central nervous system-derived spinal fluid glycoproteins having only GlcNAc at a non-reducing terminus. The present inventors have also revealed that PVL lectin, which had heretofore been considered difficult to bind to a sugar chain having α2,6 sialic acid at its non-reducing terminus, can actually bind to this sugar chain. The present invention has been completed on the basis of these novel findings and specifically provides the followings.

(1) A method for enriching or isolating a terminal GlcNAc-containing glycoprotein from a body fluid or a central neural cell derived from a test subject, comprising: (i) a removal step of removing a terminal sialic acid-containing glycoprotein from the body fluid or the central neural cell using a sialic acid-binding substance; and (ii) an isolation step of binding a terminal GlcNAc containing glycoprotein present in a sample obtained in the removal step to a GlcNAc-binding substance and isolating a formed complex.

(2) The method according to (1), further comprising the step of dissociating the complex and eluting the terminal GlcNAc-containing glycoprotein.

(3) The method according to (1) or (2), further comprising, prior to the removal step, an albumin removal step of removing albumin from the body fluid or the central neural cell using an albumin-binding substance.

(4) The method according to any of (1) to (3), wherein the sialic acid-binding substance is an anti sialic acid antibody or an active fragment thereof, or a sialic acid-binding lectin.

(5) The method according to any of (1) to (4), wherein the sialic acid is α2,6 sialic acid.

(6) The method according to (5), wherein the α2,6 sialic acid-binding lectin is selected from the group consisting of SSA lectin, SNA lectin, and TJA-I lectin.

(7) The method according to any of (1) to (6), wherein the GlcNAc-binding substance is an anti-GlcNAc antibody or an active fragment thereof, or a GlcNAc-binding lectin.

(8) The method according to (7), wherein the GlcNAc-binding lectin is PVL lectin or WGA lectin.

(9) The method according to any of (1) to (8), wherein the albumin-binding substance is Blue Sepharose, or an anti-albumin antibody or an active fragment thereof.

(10) The method according to any of (1) to (9), wherein the body fluid is spinal fluid, blood (including serum, plasma, and interstitial fluid), lymph, periradicular fluid, or a tissue or cell extract.

(11) A method for selecting an index marker for central nervous system disease, comprising: an enrichment or isolation step of enriching or isolating terminal GlcNAc-containing glycoproteins from body fluids or central neural cells derived from a control subject and an individual affected with a particular central nervous system disease, respectively, using a method according to any of (1) to (10); a measurement step of measuring the proportions of the terminal GlcNAc-containing glycoproteins obtained in the enrichment or isolation step; and a selection step of comparing the measured proportions of the corresponding terminal GlcNAc-containing glycoproteins derived from the control subject and the individual affected with a particular central nervous system disease and selecting the terminal GlcNAc-containing glycoproteins that exhibit a statistically significant quantitative difference therebetween, as an index marker for the particular central nervous system disease.

(12) A method for selecting an index marker for central nervous system disease, comprising the steps of: measuring the proportions of the terminal GlcNAc-containing glycoproteins shown in Table 1 in a control subject and an individual affected with a particular central nervous system disease; and comparing the proportions of the corresponding glycoproteins derived from the control subject and the individual affected with a particular central nervous system disease and selecting the glycoproteins that exhibit a statistically significant quantitative difference therebetween, as an index marker for the particular central nervous system disease.

TABLE 1

| No. | Glycoprotein name | Accession # | Molecular weight (Da) |
|---|---|---|---|
| 1 | Acetyl-CoA carboxylase 2 | O00763 | 279696.3 |
| 2 | Multiple EGF-like domain protein 4 | Q7Z7M0 | 254575.3 |
| 3 | α2-macroglobulin | P01023 | 163279.4 |
| 4 | Plasma protease C1 inhibitor | P05155 | 55154.7 |
| 5 | Transferrin 1 | P02787 | 77050.6 |
| 6 | Glutamate carboxylase-like protein | Q96KN2 | 56779.8 |
| 7 | α1-antichymotrypsin | P01011 | 47651.3 |
| 8 | Zinc-α2-glycoprotein | P25311 | 33872.5 |
| 9 | Inhibin βA chain | P08476 | 47442.7 |
| 10 | Prostaglandin-H2 D-isomerase (prostaglandin-D2 synthase) | P41222 | 21029.0 |
| 11 | Transthyretin | P02766 | 15887.2 |
| 12 | Cathepsin D | P07339 | 44553.0 |
| 13 | Procollagen C-endopeptidase enhancer 2 | Q15113 | 47973.0 |

(13) A kit for enriching or isolating a GlcNAc-containing glycoprotein, comprising a sialic acid-binding substance and a GlcNAc-binding substance.

(14) The kit according to (13), wherein the sialic acid-binding substance is an anti-sialic acid antibody or an active fragment thereof and/or a sialic acid-binding lectin.

(15) The kit according to (14), wherein the sialic acid is α2,6 sialic acid.

(16) The kit according to (15), wherein the α2,6 sialic acid-binding lectin is SSA lectin, SNA lectin, and/or TJA-I lectin.

(17) The kit according to any of (13) to (16), wherein the GlcNAc-binding substance is an anti-GlcNAc antibody or an active fragment thereof and/or a GlcNAc-binding lectin.

(18) The kit according to (17), wherein the GlcNAc-binding lectin is PVL lectin and/or WGA lectin.

(19) The kit according to any of (13) to (18), further comprising a buffer for complex dissociation.

(20) The kit according to (19), wherein the buffer for complex dissociation comprises GlcNAc.

(21) The kit according to any of (13) to (20), further comprising an albumin-binding substance.

(22) The kit according to (21), wherein the albumin-binding substance is an anti-albumin antibody or an active fragment thereof.

(23) An index marker for central nervous system disease, consisting of one or more glycoprotein(s) set forth in Table 1 above (except for transferrin 1 set forth in Table 1 when the central nervous system disease is idiopathic normal pressure hydrocephalus) or fragment(s) thereof, the glycoproteins each comprising a GlcNAc residue at a non-reducing terminus and having an α2,6 sialic acid-free sugar chain.

(24) The index marker for central nervous system disease according to (23), wherein the central nervous system disease is neuromyelitis optica.

(25) The index marker for central nervous system disease according to (23), wherein the central nervous system disease is Guillain-Barre syndrome.

(26) The index marker for central nervous system disease according to (23), wherein the central nervous system disease is acute disseminated encephalomyelitis.

(27) The index marker for central nervous system disease according to (23), wherein the central nervous system disease is encephalopathy.

(28) The index marker for central nervous system disease according to any of (24) to (27), wherein the index marker for central nervous system disease is α2-macroglobulin set forth in Table 1.

(29) A method comprising detecting an one or more index marker(s) for central nervous system disease according to (23) from a body fluid or a central neural cell derived from a test subject and determining the presence or absence of a particular central nervous system disease developed in the test subject on the basis of the detection results.

(30) The method according to (29), wherein the particular central nervous system disease is neuromyelitis optica.

(31) The method according to (30), wherein the index marker for central nervous system disease to be detected is α2-macroglobulin set forth in Table 1.

The present specification encompasses the contents described in the specification and/or drawings of Japanese Patent Application No. 2010-280753 on which the priority of the present application is based.

Advantageous Effects of Invention

The enrichment or isolation method of the present invention and the kit based on the method can conveniently and efficiently enrich, isolate, and select a central nervous system-derived glycoprotein present in a trace amount in a body fluid and/or a central neural cell.

The method for selecting an index marker for central nervous system disease according to the present invention can select and isolate a glycoprotein as a novel index marker for central nervous system disease. Use of the index marker for the particular central nervous system disease thus obtained permits early, simple, and low invasive diagnosis of onset of the disease.

BRIEF DESCRIPTION OF DRAWINGS

FIG. 5A shows the positions of various lectins on the microarray. FIGS. 5B and 5C show results obtained using the lectin microarray from spinal fluid and from fraction D (enriched fraction), which was an eluted fraction from a PVL column, respectively.

DESCRIPTION OF EMBODIMENTS

Figure 1:
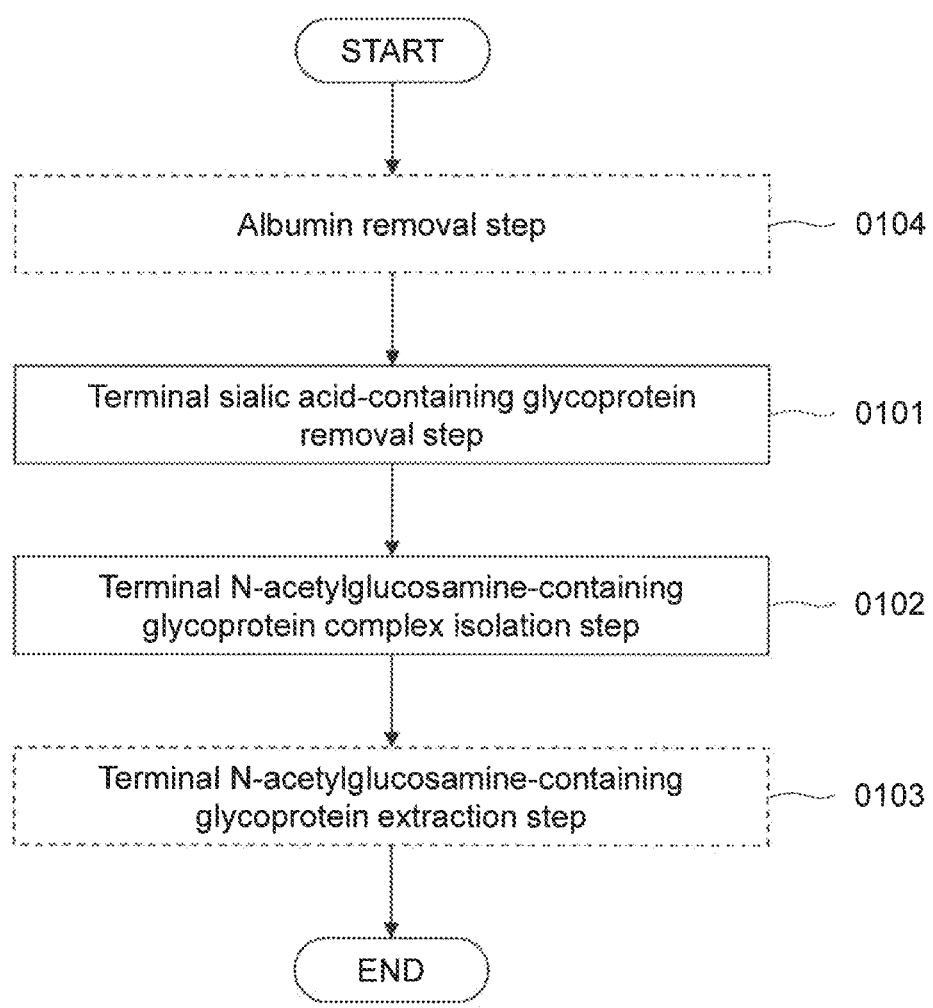
FIG. 1 is a flow chart schematically showing the method of the first embodiment of the present invention. Each step boxed by the broken line represents an optional step.

Embodiment 1: Method for Enriching or Isolating Terminal GlcNAc-Containing Glycoprotein (Summary)

The first embodiment of the present invention relates to a method for enriching or isolating a terminal GlcNAc (N-acetylglucosamine)-containing glycoprotein from a body fluid or a central neural cell.

The "terminal GlcNAc-containing glycoprotein" is a glycoprotein having a GlcNAc residue at a non-reducing terminus of the sugar chain. The "terminal GlcNAc-containing glycoprotein" described in the present specification particularly refers to a spinal fluid glycoprotein. The "non-reducing terminus of the sugar chain" refers to, in the structure of the sugar chain alone (excluding the protein moiety), a terminal sugar other than a sugar chain terminus that exhibits reducibility (reducing terminus). Reducible sugars take hemiacetal (or ketal) structures. For example, glucose takes a cyclic structure through the reaction between an aldehyde group at position 1 and a hydroxyl group at position 5. Even in a sugar chain, the aldehyde group can be regenerated through reverse reaction in the presence of a conserved hydroxyl group on carbon at position 1 of the cyclic structure so that the resulting open-chain glucose can exhibit reducibility. As in the non-reducing terminal sugar of a sugar chain, however, this hydroxyl group at position 1 forms a glycoside bond, which in turn hinders the reaction for generating the aldehyde group. The resulting sugar does not exhibit reducibility. In other words, a reducing terminal sugar has a free hydroxy group at position 1 (1-hydroxyl group). Typically, such a reducing terminal sugar is bound with the protein.

In the present specification, the "spinal fluid glycoprotein" refers to a glycoprotein that is expressed in cells of the central nervous system such as the brain and/or the spinal cord, found mainly in spinal fluid, and has a GlcNAc residue at a non-reducing terminus of the sugar chain. The "spinal fluid glycoprotein" also includes a glycoprotein having so-called bisecting GlcNAc (GlcNAc bound through a β1-4 bond to Man in the trisaccharide structure Manβ1-4GlcNAcβ1-4GlcNAc at a reducing terminus of N-glycan) or core fucose (fucose bound through a α1-6 bond to GlcNAc at a reducing terminus of the Manβ1-4GlcNAcβ1-4GlcNAc). The spinal fluid glycoprotein, however, does not include a glycoprotein that has sialic acid residue at a non-reducing terminus of the sugar chain, even if the glycoprotein has a GlcNAc residue at another non-reducing terminus of the sugar chain. In the present specification, such a glycoprotein having one or more sialic acid residue(s) at a non-reducing terminus belongs to a serum glycoprotein described later.

The number of terminal GlcNAc residues is not particularly limited. For example, the glycoprotein may have one terminal GlcNAc residue or may have a plurality of terminal GlcNAc residues if its sugar chain has branches. In this context, the term "plurality" refers to, for example, two or more, three or more, or four or more.

The method of this embodiment comprises, as shown in FIG. 1, a terminal sialic acid-containing glycoprotein removal step (0101) and a terminal GlcNAc-containing glycoprotein complex isolation step (0102). In this embodiment, the method may optionally comprise a terminal GlcNAc-containing glycoprotein extraction step (0103) after the complex isolation step (0102). The method may further optionally comprise an albumin removal step (0104) prior to the removal step (0101). Hereinafter, each step will be described specifically.

1-1. Terminal Sialic Acid-Containing Glycoprotein Removal Step.

(Constitution)

The "terminal sialic acid-containing glycoprotein removal step" (0101) (hereinafter, simply referred to as a "removal step") refers to the step of removing a terminal sialic acid-containing glycoprotein from the body fluid or central neural cells of a test subject using a sialic acid-binding substance.

In the present specification, the "terminal sialic acid-containing glycoprotein" refers to a glycoprotein having at least one sialic acid residue at a non-reducing terminus of the sugar chain. Since the glycoprotein having a sugar chain with such a structure is usually found in large amounts in serum, the "terminal sialic acid-containing glycoprotein" is also referred to as a "serum glycoprotein" in the present specification. As mentioned above, however, a large number of serum proteins are also leaked into spinal fluid. Thus, the serum glycoprotein is not a serum-specific protein and may be found as a major protein component even in spinal fluid.

The "sialic acid" is one type of acidic sugar present at a sugar chain terminus and refers to a substance having a structure in which the amino group or hydroxyl group of neuraminic acid is replaced by a different functional group. Examples thereof include N-acetylneuraminic acid (NeuAc).

Examples of the binding pattern of the sialic acid linked to the sugar chain in the present specification include, but not particularly limited to, an α2,6-sialylated (sialic acid having an α2,6 bond; Sia-α2,6-Gal) sugar chain. The number of terminal sialic acid residues in the sugar chain of the terminal sialic acid-containing glycoprotein is not particularly limited. For example, the glycoprotein may have one terminal sialic acid residue or may have a plurality of terminal sialic acid residues if its sugar chain has branches. In this context, the term "plurality" refers to two or more and may be three or more or four or more.

The "sialic acid-binding substance" refers to a substance that binds with affinity, preferably with specificity, to the sialic acid. Hence, the sialic acid-binding substance does not bind to the terminal GlcNAc-containing glycoprotein of the present invention free from terminal sialic acid in the sugar chain. The binding may be any of reversible binding and irreversible binding. Examples of the sialic acid-binding substance include an anti-sialic acid antibody and an active fragment thereof, and a sialic acid-binding lectin.

The "anti-sialic acid antibody" refers to a sugar chain-directed antibody capable of recognizing sialic acid and specifically binding thereto. In the present specification, the "antibody" refers to an immunoglobulin, a chimeric antibody, a humanized antibody, or a synthetic antibody (Diabody, etc.). The immunoglobulin used as the antibody may be any of polyclonal and monoclonal antibodies. Specific examples of the anti-sialic acid antibody include an anti-α2,6 sialic acid antibody that recognizes an α2,6-sialylated sugar chain and specifically binds thereto.

In the present specification, the "active fragment thereof" is a partial region of the antibody mentioned above and refers to a polypeptide chain having activity substantially equivalent to the antigen-specific binding activity of the antibody, or a complex of the polypeptide chain. The active fragment corresponds to, for example, a polypeptide chain having at least one light chain variable region ($V_L$), and at least one heavy chain variable region ($V_H$), or a complex of the polypeptide chain. Specific examples thereof include antibody fragments finned by the cleavage of an immunoglobulin with various peptidases. More specifically, the active fragment corresponds to, for example, Fab, F(ab')$_2$, or Fab'.

The anti-sialic acid antibody of the present invention can be derived from every animal including birds and mammals. Examples thereof include mice, rats, guinea pigs, rabbits, goat, donkeys, sheep, camels, horses, chickens, and humans.

Such an anti-sialic acid antibody can be prepared according to a method known in the art. See, for example, the method described in Patent Literature 3. Alternatively, a commercially available antibody may be used.

The "sialic acid-binding lectin" refers to a protein (other than antibodies) having binding activity against the terminal sialic acid-containing glycoprotein, i.e., the serum glycoprotein. Its type, etc. is not particularly limited as long as the lectin is capable of recognizing sialic acid at a non-reducing terminus of the glycoprotein and binding thereto. Examples thereof include α2,6 sialic acid-binding lectin that can recognize a glycoprotein having α2,6 sialic acid at a terminus of the sugar chain and bind thereto. Specific examples of the α2,6 sialic acid-binding lectin include *Sambucus sieboldiana*-derived agglutinin (SSA) lectin, *Sambucus nigra*-derived agglutinin (SNA) lectin, and *Trichosanthes japonica*-derived type I agglutinin (TJA-I) lectin. Such α2,6 sialic acid-binding lectin used may be commercially available lectin. For example, 300177 from Seikagaku Biobusiness Corp. or J1001014 from Medical & Biological Laboratories Co., Ltd. (MBL) can be used as the SSA lectin. L6890 Lectin from *Sambucus nigra* (elder) from Sigma-Aldrich Corp. can be used as the SNA lectin. 300186 from Seikagaku Biobusiness Corp. can be used as the TJA-I lectin.

In the present specification, the "test subject" refers to an individual that is subjected to a test, i.e., a vertebrate, preferably a mammal, more preferably a human that provides a body fluid or a central neural cell. The test subject may be any of an individual having a certain disease and a healthy individual.

The "body fluid" refers to a biological sample in a liquid state that is collected from the test subject and may contain the terminal GlcNAc-containing glycoprotein. Examples thereof include spinal fluid, blood (including serum, plasma, and interstitial fluid), lymph, periradicular fluid, an extract of each tissue or cell, lacrimal fluid, nasal discharge, saliva, urine, vaginal fluid, and seminal fluid. Spinal fluid, blood, lymph, or periradicular fluid is preferred. The body fluid used may be directly collected from the test subject or may be diluted or concentrated, if necessary, or supplemented with an anticoagulant such as heparin. The body fluid can be collected on the basis of a method known in the art. For example, blood or lymph can be collected according to a heretofore known blood collection method. Specifically, peripheral blood can be collected by injection from the vein or the like in a peripheral portion. Alternatively, spinal fluid can be collected by heretofore known lumbar puncture, while cord blood can be collected by the injection of a needle to the postpartum umbilical cord before placenta delivery. The body fluid may be used immediately after collection or may be used after being cryopreserved or refrigerated for a given time and then treated (e.g., thawed) if necessary. In this embodiment, spinal fluid, for example, can be used in a volume of at least 0.1 mL, preferably at least 1 mL, more preferably at least 10 mL, to enrich or isolate the terminal GlcNAc-containing glycoprotein in an amount sufficient for detection. Alternatively, blood can be used in a volume of at least 1 mL, preferably at least 10 mL, more preferably at least 30 mL, to enrich or isolate the terminal GlcNAc-containing glycoprotein in an amount sufficient for detection.

The "central neural cell" refers to a brain (including the cerebrum, mesencephalon, diencephalon, pons, cerebellum, and medulla oblongata) cell or spinal cord cell collected from the test subject, or a tissue which is an aggregate of the cells. The central neural cell is preferably homogenized in advance and used as a cell extract for the method of this embodiment. For this homogenization, a surfactant (NP-40, Triton X-100, etc.) is added in order to extract a membrane-binding spinal fluid glycoprotein. If necessary, a medium such as saline or a PBS buffer may be added.

(Methodology)

This step can be achieved by binding a terminal sialic acid-containing glycoprotein contained in a body fluid or a central neural cell derived from a test subject (hereinafter, they are collectively referred to as a "body fluid, etc.") to a sialic acid-binding substance and removing the formed complex from the body fluid, etc.

The complex can be formed by a method of contacting the body fluid, etc. with the sialic acid-binding substance. Examples thereof include a method involving mixing a fluid containing the sialic acid-binding substance with the body fluid, etc. The formed complex can be removed from the body fluid, etc. by any method known in the art. Examples thereof include a method involving contacting the body fluid, etc. with a sialic acid-binding substance immobilized on the surface of a carrier or labeled with a compound and then removing the formed complex on the basis of the character of the carrier or the compound.

The "carrier" includes a high-molecular-weight polysaccharide support (e.g., Sepharose or Sephadex), magnetic beads, silica, glass, a metal (e.g., gold, platinum, or silver), a plastic resin (e.g., plastic such as polystyrene, or polyacrylamide), ceramic, latex, etc. The shape of the carrier is not particularly limited and is preferably a shape with a large surface area. This is because such a large surface area increases opportunities for the contact between the sialic acid-binding substance immobilized on the surface of the carrier and the terminal sialic acid-containing glycoprotein in the body fluid, etc., and permits more efficient formation of the complex. The shape is preferably, for example, a shape of beads, porous particles, or a fiber assembly. A shape that is easily packed into a column or the like is more preferred.

The "compound" includes a fluorescent dye (e.g., Cy3, Cy5, FAM, HEX, VIC, or TAMRA), a luminescent substance, or biotin or (strept)avidin, etc.

The immobilization of the sialic acid-binding substance onto the carrier or the labeling thereof with the compound according to the present invention is preferably irreversible binding, i.e., binding that is not dissociated through reverse reaction after being once formed or binding that is dissociated only to a negligible degree. Examples of such irreversible binding include a covalent bond through chemical reaction such as nucleophilic addition reaction, nucleophilic substitution reaction, or electrophilic substitution reaction between functional groups, and a noncovalent bond through high affinity. The covalent bond, for example, a direct bond, through chemical reaction can be achieved by modifying the sialic acid-binding substance and the carrier or the compound with appropriate functional groups, respectively, and forming a covalent bond through chemical reaction between the functional groups. In this case, the functional groups can be combined so as to form the covalent bond. Examples of such a combination include amino and aldehyde groups, thiol and maleimide groups, azide and acetylene groups, azide and amino groups, hydrazine and ketone groups, and hydrazine and aldehyde groups. Such a method for forming a covalent bond through chemical reaction is a technique well known by those skilled in the art.

The complex formed by the binding of the terminal sialic acid-containing glycoprotein to the sialic acid-binding substance can be isolated by an appropriate heretofore known method using the character of the carrier or the compound. In this context, the "character" refers to a property unique to the carrier or the compound. Examples thereof include magnetic force, specific gravity, fluorescence, luminescence, and affinity. As a specific example, column chromatography (including HPLC) can be used for a sialic acid-binding substance immobilized on a high-molecular-weight polysaccharide support, silica, or the like. Specifically, the high-molecular-weight polysaccharide support with the immobilized sialic acid-binding substance is packed as a resin into a column. Then, the body fluid, etc. is applied to the column. A sample liquid eluted from the column, i.e., remaining fractions after capture of the terminal sialic acid-containing glycoprotein by the resin, can be recovered. Alternatively, in the case of using a sialic acid-binding substance immobilized on a carrier such as glass heads or Sephadex beads, the beads with the immobilized sialic acid-binding substance are added to the body fluid, etc. and stirred, if necessary. Then, sialic acid-binding substance-immobilized beads bound with the terminal sialic acid-containing glycoprotein are precipitated by centrifugation using the specific gravity of the carrier. The resulting upper-layer liquid can be recovered. In the case of using a sialic acid-binding substance immobilized on magnetic beads, the sialic acid-binding substance-immobilized magnetic beads are added to the body fluid, etc. and, for example, stirred, if necessary. Then, sialic acid-binding substance-immobilized beads bound with the terminal sialic acid-containing glycoprotein are removed using magnetic force. The resulting liquid portion can be recovered. Alternatively, in the case of using a sialic acid-binding substance labeled with a compound such as a fluorescent dye or a luminescent substance, the labeled sialic acid-binding substance is added to the body fluid, etc. and stirred, if necessary. Then, the complex of the terminal sialic acid-containing glycoprotein bound with the labeled sialic acid-binding substance can be separated and removed using a cell sorter or flow cytometry. These methods may follow their respective methods known in the art.

In this step, the same removal method may be performed a plurality of times, for example, twice, three times, four times, five times, or six times, or two or more different removal methods may be combined to thereby more reliably remove the terminal sialic acid-containing glycoprotein in the body fluid, etc.

As mentioned above, it has heretofore been the common general knowledge of the art that PVL lectin strongly binds to non-reducing terminal GlcNAc and hardly binds to non-reducing terminal Sia-α2,6-Gal, which is a major sugar chain terminus of a blood glycoprotein. Thus, those skilled in the art have assumed that a spinal fluid glycoprotein is enriched using PVL lectin alone with the aim of developing a simpler method. Nonetheless, the present inventors have revealed that, in actuality, PVL lectin also binds to non-reducing terminal Sia-α2,6-Gal and demonstrated that this step is essential for enriching a spinal fluid glycoprotein.

This step can remove the terminal sialic acid-containing glycoprotein, i.e., the serum glycoprotein, contained in the body fluid or the central neural cell.

1-2. Terminal GlcNAc-Containing Glycoprotein Complex Isolation Step.

(Constitution)

The "terminal GlcNAc-containing glycoprotein complex isolation step" (0102) (hereinafter, simply referred to as a "complex isolation step") refers to the step of binding a terminal GlcNAc-containing glycoprotein present in a sample obtained in the removal step (0101) to a GlcNAc-binding substance and isolating and recovering the formed complex.

The sample obtained after the removal step (0101) contains no terminal sialic acid-containing glycoprotein or contains only an exceedingly trace amount of this glycoprotein. Hence, a glycoprotein having a GlcNAc residue at a sugar chain terminus in this sample is the spinal fluid glycoprotein intended by the present invention, as a rule. Thus, the feature of this step is that the terminal GlcNAc-containing glycoprotein is isolated in the form of a complex with the GlcNAc-binding substance from the sample that has undergone the removal step (0101).

In the present specification, the "GlcNAc-binding substance" refers to a substance that binds with affinity, preferably with specificity, to GlcNAc or a GlcNAc-terminated sugar chain. The binding between GlcNAc and the GlcNAc-binding substance is preferably reversible binding if a sample solution obtained in this step is subjected to the terminal GlcNAc-containing glycoprotein extraction step described later. Examples of the GlcNAc-binding substance include an anti-GlcNAc antibody and an active fragment thereof, and a GlcNAc-binding lectin.

The "anti-GlcNAc antibody" refers to a sugar chain-directed antibody capable of specifically recognizing GlcNAc and binding thereto. This anti-GlcNAc antibody can be prepared according to a method known in the art. See, for example, the method described in Patent Literature 3. For example, OMB4 (Ozawa, H et al., Archives of Biochemistry and Biophysics 1997, vol. 342 (1), p. 48-57) can be used.

The "GlcNAc-binding lectin" refers to a protein (other than antibodies) having binding activity against GlcNAc or the glycoprotein having GlcNAc at a sugar chain terminus. Its type, etc. is not particularly limited as long as the lectin is capable of recognizing GlcNAc at a terminus of the sugar chain and binding thereto. Examples thereof include *Psathyrella velutina*-derived PVL lectin and bread wheat-derived WGA lectin. The GlcNAc-binding lectin used may be commercially available lectin. For example, 165-1759 *Psathyrella Velutina* Lectin from Wako Pure Chemical Industries, Ltd. or Recombinant PVL from Medical & Biological Laboratories Co., Ltd. (MBL) can be used as the PVL lectin. Alternatively, 300191 from Seikagaku Biobusiness Corp. or J1001016 from Medical & Biological Laboratories Co., Ltd. (MBL) can be used as the WGA lectin.

(Methodology)

This step can be achieved by binding a terminal GlcNAc-containing glycoprotein contained in the sample solution obtained after the removal step to a GlcNAc-binding substance and recovering the formed complex.

The complex is formed according to the method described in the removal step. Also, the formed complex of the terminal GlcNAc-containing glycoprotein and the GlcNAc-binding substance is recovered according to the method described in the removal step, as a rule. This step, however, differs from the removal step in that the formed complex of the terminal GlcNAc-containing glycoprotein and the GlcNAc-binding substance is recovered and the remaining sample solution is removed.

In this step, the sample solution after the recovery of the complex may be further subjected to the same isolating method or two or more different isolating methods a plurality of times to thereby more reliably recover the terminal GlcNAc-containing glycoprotein in the sample solution.

The complex of the terminal GlcNAc-containing glycoprotein and the GlcNAc-binding substance thus recovered may be washed several times with an appropriate buffer (e.g., a PBS buffer) to remove contaminating impurities.

This step can selectively enrich or isolate the terminal GlcNAc-containing glycoprotein contained in the body fluid or the central neural cell, i.e., the spinal fluid glycoprotein.

1-3. Terminal GlcNAc-Containing Glycoprotein Extraction Step.

(Constitution)

The "terminal GlcNAc-containing glycoprotein extraction step" (0103) (hereinafter, simply referred to as an "extraction step") refers to the step of dissociating the complex of the terminal GlcNAc-containing glycoprotein and the GlcNAc-binding substance and eluting the terminal GlcNAc-containing glycoprotein. This step is an optional step that can be selected in the present invention.

(Methodology)

The terminal GlcNAc-containing glycoprotein and the GlcNAc-binding substance constituting the complex can be dissociated therebetween by a method known in the art according to the property of the GlcNAc-binding substance.

For example, in the case of using an anti-GlcNAc antibody as the GlcNAc-binding substance, the terminal GlcNAc-containing glycoprotein can be dissociated from the anti-GlcNAc antibody by the competition therebetween for added GlcNAc or the like having the same hapten.

Alternatively, the complex may be dissociated under high-salt concentration conditions (e.g., $Mg^{2+}>2$ M) or strongly acidic conditions (e.g., Gly-HCl pH 3>).

In the case of using a GlcNAc-binding lectin as the GlcNAc-binding substance, the complex can be dissociated by the addition of a hapten sugar GlcNAc.

This step can isolate and obtain only the terminal GlcNAc-containing glycoprotein from the complex.

1-4. Albumin Removal Step.

(Constitution)

The "albumin removal step" (0104) refers to the step of removing albumin contained in the body fluid, etc. using an albumin-binding substance prior to the removal step. This step is also an optional step that can be selected in the present invention.

In the present specification, the "albumin" is albumin contained in the body fluid, etc. and means mainly serum albumin.

(Methodology)

The basic principle of this step follows that of the removal step (0101). Specifically, this step can be achieved by contacting an albumin-binding substance with the body fluid, etc. to form a complex of the albumin-binding substance in the body fluid and the albumin-binding substance, and then removing the complex.

The "albumin-binding substance" refers to a substance that binds with affinity, preferably with specificity, to the albumin. This binding may be any of reversible binding and irreversible binding. Desirably, this binding is irreversible for preventing once bound albumin from being dissociated and mixed again into the body fluid, etc.

Examples of the albumin-binding substance include an anti-albumin antibody and an active fragment thereof.

The "anti-albumin antibody" refers to an antibody capable of recognizing albumin, mainly serum albumin, and binding thereto. This antibody used may be a commercially available antibody. For example, A80-129A Human Albumin Antibody Affinity Purified from Bethyl Laboratories, Inc. or KR-002 antibody from Cosmo Bio Co., Ltd. can be used.

The complex of the albumin in the body fluid, etc. and the albumin-binding substance is formed and/or the formed complex of the albumin and the albumin-binding substance is removed according to the methods described in the removal step (0101).

This step can subject the body fluid, etc. from which an impurity albumin has been removed to the terminal sialic acid-containing glycoprotein removal step.

1-5. Effect

According to this embodiment, the terminal GlcNAc-containing glycoprotein, i.e., the spinal fluid glycoprotein, which has heretofore been exceedingly difficult to detect, can be enriched or isolated efficiently and selectively from a body fluid, etc.

Embodiment 2: Method for Selecting Index Marker for Central Nervous System Disease (Summary and Constitution)

The second embodiment of the present invention relates to a method for selecting an index marker for central nervous system disease.

The method of this embodiment involves: efficiently removing blood glycoproteins present in large amounts in a body fluid, etc. i.e., a terminal sialic acid-containing glycoprotein group, using the method of Embodiment 1 to enrich or isolate spinal fluid glycoproteins, i.e., a terminal GlcNAc-containing glycoprotein group, of interest; and then selecting a terminal GlcNAc-containing glycoprotein serving as an index marker for a particular central nervous system disease from the obtained terminal GlcNAc-containing glycoprotein group.

The "index marker" refers to a substance having a character that is objectively measured and evaluated as an index for a pathological process or a pharmacological response to therapeutic intervention. Thus, in the present specification, the "index marker for central nervous system disease" means a glycoprotein having a character that can be objectively measured and evaluated in response to the presence or absence of a particular central nervous system disease developed or the like or severity thereof, or a fragment of the glycoprotein. Specific examples thereof will be described later in Embodiment 4.

In the present specification, the "central nervous system disease" refers to a disease that is caused by the functional abnormality and/or morphological abnormality (including developmental abnormality) of the brain and/or the spinal cord. Examples of neurodegenerative disease include Alzheimer's disease (AD; and its prodromal phase mild cognitive impairment), frontotemporal dementia, dementia with Lewy bodies, Parkinson's disease, progressive supranuclear palsy, and corticobasal degeneration. Examples of metabolic disorder include idiopathic normal pressure hydrocephalus (iNPH), obstructive hydrocephalus, and infectious or metabolic encephalopathy. Examples of autoimmune-related disease include multiple sclerosis (MS), neuromyelitis optica (NMO), Guillain-Barre syndrome (which often affects peripheral motor nerves, whereas its pharyngeal-cervical-brachial variant damages cranial nerves), and acute disseminated encephalomyelitis (ADEM). Examples of mental disease include schizophrenia, bipolar disorder, and major depression. Examples of neoplastic disease include neuroepithelial tissue tumor (glioma, neuronal tumor, etc.), nerve sheath tumor (neurilemmoma, neurofibroma, etc.), meningeal tumor (meningioma and other mesenchymal neoplasms), sellar tumor, and metastatic tumor. Examples of infectious disease include bacterial or viral encephalomeningitis.

Figure 2:
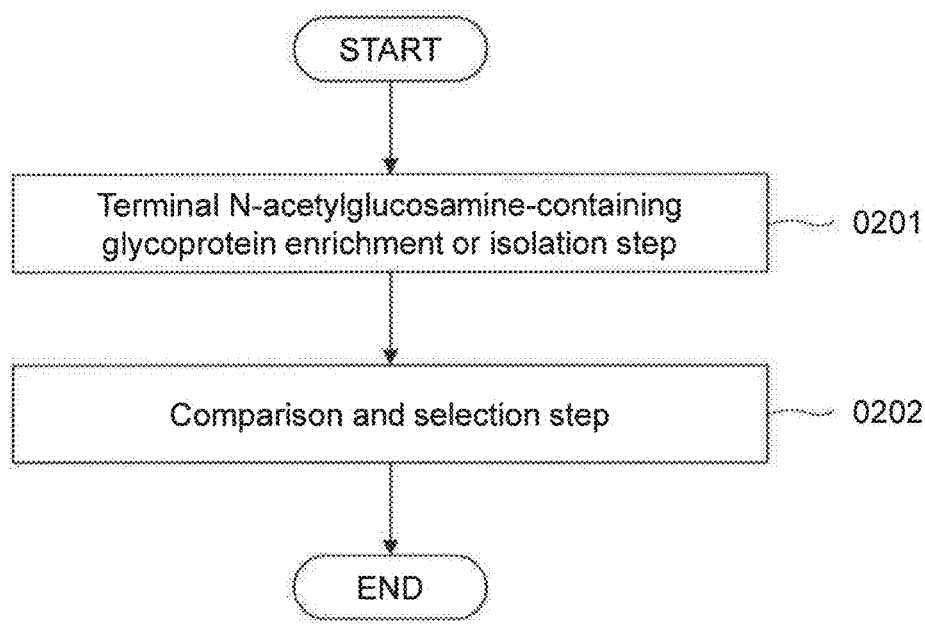
FIG. 2 is a flow chart schematically showing the method of the second embodiment of the present invention.

The method of this embodiment comprises, as shown in FIG. 2, a terminal GlcNAc-containing glycoprotein enrichment or isolation step (0201) and a comparison and selection step (0202). Hereinafter, the methodology of each step will be described specifically.

(Methodology)

2-1. Terminal GlcNAc-Containing Glycoprotein Enrichment or Isolation Step.

The "terminal GlcNAc-containing glycoprotein enrichment or isolation step" (0201) refers to the step of isolating terminal GlcNAc-containing glycoprotein groups from a control subject-derived body fluid, etc. (hereinafter, referred to as a "control subject sample") and from the body fluid, etc. of an individual affected with a particular central nervous system disease (hereinafter referred to as an "affected individual sample"), respectively, using the method of Embodiment 1.

In the present specification, the "control subject" refers to an individual unaffected with a target central nervous system disease (hereinafter, referred to as a "target disease") at the time of collection of the control subject sample. The control subject for the target disease-affected individual may be, for example, not only an individual affected with no central nervous system disease, such as a healthy individual, but an individual affected with no target disease but affected with a different central nervous system disease. An individual affected with no target disease but affected with a different central nervous system disease very similar in symptom to the particular central nervous system disease is particularly preferred as the control subject according to this embodiment. The combination of a target disease with a different central nervous system disease that is difficult to distinguish therefrom due to their very similar symptoms will be described below.

Of the diseases described above, the mental disease is symptomatologically diagnosed. Particularly, major depression and bipolar disorder (depressive and manic states are repeated) are difficult to distinguish therebetween. Thus, a novel diagnostic marker has been demanded for the general mental disease. Neoplastic disease differs in neurological symptom depending on the site of its origin. In addition, the size of its lesion can be measured easily by a morphological test. The prognosis of the neoplastic disease, however, depends on the infiltration of tumor cells. There exist few biomarkers that reflect such a biological property.

Multiple sclerosis (MS) is known as a typical autoimmune demyelinating disease. MS is a disease commonly found in Caucasian females. The number of patients with this disease reportedly reaches 400,000 (one in 750 people) in the USA and 2,500,000 around the world. In Japan, MS had previously been regarded as a disease with an incidence as low as 1/10,000 (one in 10,000 people). Its incidence, however, has significantly increased in recent years along with the westernization of lifestyle (particularly, diet).

Neuromyelitis optica (Devic's disease) had historically been regarded as a subtype of multiple sclerosis. In 2005, however, the autoantibody of a neuromyelitis optica patient was shown to recognize aquaporin-4 of a water channel, indicating that this disease is independent of multiple sclerosis. Since then, definite diagnosis based on the presence of this antibody has been conducted. Unfortunately, this antibody is technically difficult to measure and can be measured only by four laboratories in Japan with a positive rate significantly differing from 60 to 80% among facilities. The acute stages of NMO and MS require a strong formulation such as steroid for treatment. At their chronic stages, interferon $\beta$ is used for MS in order to prevent recurrence, whereas a small amount of a steroid drug or an immunosuppressant is used for NMO instead of interferon $\beta$ that may exacerbate the symptom of NMO. Thus, the differential diagnosis between these diseases is an exceedingly important challenge because the diseases differ in treatment method. Hence, a diagnostic marker that permits accurate diagnosis of these diseases has been demanded.

Although some of the central nervous system diseases listed above can be diagnosed morphologically (by MRI or CT scan) along with their progression, most of the diseases are difficult to distinguish at their initial stages. For example, Parkinson's disease, progressive supranuclear palsy, and corticobasal degeneration exhibit very similar gait abnormalities and hardly vary morphologically. The initial stage of Alzheimer's disease is not easy to distinguish from the initial condition of dementia with Lewy bodies or frontotemporal dementia. Particularly, in frontotemporal dementia, phosphorylated tau protein exhibits an increased level in spinal fluid, as in Alzheimer's disease. Thus, a conventional differential diagnosis marker considered most effective cannot be used. Although remarkable morphological changes such as dementia and ventricular dilatation (brain atrophy) are seen in advanced Alzheimer's disease, these two symptoms are also observed in idiopathic normal pressure hydrocephalus. In fact, only 1200 people (0.4% of the predicted number of patients) yearly undergo the radical surgery of idiopathic normal pressure hydrocephalus described later, though the number of patients with this disease is estimated 310,000. This means that many idiopathic normal pressure hydrocephalus patients are likely to be misdiagnosed as Alzheimer's disease and left without benefiting from treatment. Idiopathic normal pressure hydrocephalus is caused by an excess of spinal fluid and thus, can be cured by simple minor surgery (e.g., ventriculoperitoneal shunt using a tube for bypassing a communication between the cerebral ventricle and the peritoneum) to drain the excess of spinal fluid. Accordingly, accurate diagnosis thereof has been demanded because this dementia is "curable".

The discovery of markers for the diseases described above will be described in detail Examples below.

The individual is not necessarily required to be a living body as long as the individual has just died and, obviously, his or her central nervous system is not affected. In the present invention, the individual is preferably a mammal, more preferably a primate, particularly preferably a human.

The details of methods for this step are described above in Embodiment 1, so that the detailed description thereof is omitted here. One example of the terminal GlcNAc-containing glycoprotein group, i.e., the spinal fluid glycoprotein group, obtained by this step includes the spinal fluid glycoprotein group of Table 1 isolated in Example 2 described later. All of the glycoproteins in this group can become candidates for the index marker for central nervous system disease of this embodiment.

2-2. Comparison and Selection Step.

The "comparison and selection step" (0202) refers to the step of quantifying the terminal GlcNAc-containing glycoproteins obtained from the control subject sample and the affected individual sample, respectively, in the preceding step, comparing the proportions of the corresponding terminal GlcNAc-containing glycoproteins, and selecting the terminal GlcNAc-containing glycoproteins that exhibit a statistically significant quantitative difference therebetween, as an index marker for the particular central nervous system disease based on the affected individual sample.

The "proportion" is the amount of a particular terminal GlcNAc-containing glycoprotein in the terminal GlcNAc-containing glycoprotein group obtained in the preceding step and may be a relative amount such as concentration or may be an absolute amount such as weight or volume.

In this step, first, the terminal GlcNAc-containing glycoproteins included in the terminal GlcNAc-containing glycoprotein groups obtained from the control subject sample and the affected individual sample, respectively, in the preceding step are quantified. Methods for such detection and quantification are not particularly limited. For example, mass spectrometry, antigen-antibody reaction method, or electrophoresis can be used.

The "mass spectrometry" encompasses every heretofore known quantification method using a mass spectrometer. Examples thereof include high-performance liquid chromatography-mass spectrometry (LC-MS), high-performance liquid chromatography-tandem mass spectrometry (LC-MS/MS), gas chromatography-mass spectrometry (GC-MS), gas chromatography-tandem mass spectrometry (GC-MS/MS), capillary electrophoresis-mass spectrometry (CE-MS), and ICP-mass spectrometry (ICP-MS).

The "antigen-antibody reaction method" encompasses every heretofore known quantification method using an antibody. Examples thereof include enzyme-linked immunosorbent assay (ELISA) and methods equivalent thereto, flow cytometry, surface plasmon resonance (SPR) method, and quartz crystal microbalance (QCM) method.

The "electrophoresis" encompasses every heretofore known quantification method based on electrophoresis. Examples thereof include two-dimensional electrophoresis.

These detection or quantification methods are techniques known in the art and thus, can be performed according to their respective heretofore known methods.

Next, the results of quantifying the proportions of the corresponding terminal GlcNAc-containing glycoproteins of the control subject and the affected individual, i.e., the terminal GlcNAc-containing glycoproteins of the same type therebetween, are compared. In this case, a heretofore known protein that is included in the terminal GlcNAc-containing glycoprotein group and expected to have no quantitative difference in expression between the control subject and the affected individual can be used as an internal control to thereby correct the quantification results of the control subject and the affected individual. Examples of such a protein for an internal control include albumin. As a result of the comparison, the terminal GlcNAc-containing glycoproteins that exhibit a statistically significant quantitative difference therebetween are selected as an index marker for the particular central nervous system disease. The selected index marker for central nervous system disease may be an index marker specific for the particular central nervous system disease or may be an index marker for a plurality of central nervous system diseases.

The term "statistically significant" means that there is a significant difference between the two corresponding terminal GlcNAc-containing glycoproteins when their quantitative difference is statistically processed. Specific examples thereof include a difference with a significance level smaller than 5%, 1%, or 0.1%. The test method for statistical processing is not particularly limited, and a heretofore known test method capable of determining the presence or absence of significance can be used appropriately. For example, a Student's t test method or a multiple comparison test method can be used. See the literatures (Kanji Suzuki, Toukeigaku No Kiso (Basic of Statistics in English); and Yasushi Nagata, et al., Toukeiteki Taiyuhikakuhou No Kiso (Basic of Statistical Multiple Comparison Method in English)).

The statistically significant quantitative difference is a difference of 1.3 or more times, preferably 1.5 or more times, more preferably 1.7 or more times, further preferably 2 or more times, between the samples. The statistically significant quantitative difference may be the proportion of the particular terminal GlcNAc-containing glycoprotein derived from the affected individual larger or smaller than that of the terminal GlcNAc-containing glycoprotein derived from the control subject. This is because any terminal GlcNAc-containing glycoprotein that specifically increases or decreases in a particular central nervous system disease can become a candidate for the index marker of the present invention. Particularly, in the detection or quantification results, a terminal GlcNAc-containing glycoprotein that is present in the body fluid, etc. of one of the control subject and the affected individual and absent in the body fluid, etc. of the other individual can serve as a preferable index marker for the particular central nervous system disease.

The proportions of various glycoproteins in the terminal GlcNAc-containing glycoprotein group obtained from the control subject sample may be stored in a database. In such a case, only the body fluid, etc. derived from the individual affected with central nervous system disease can be analyzed as long as the terminal GlcNAc-containing glycoprotein enrichment or isolation step is carried out under the same conditions thereas. This approach is convenient because the analysis of the control subject-derived body fluid, etc. in each test can be omitted.

According to this embodiment, a terminal GlcNAc-containing glycoprotein that can serve as an index marker for central nervous system disease, which has heretofore been difficult to search for, can be selected easily and efficiently from the body fluid, particularly, the spinal fluid or the central neural cell, of an individual affected with the central nervous system disease.

When a plurality of terminal GlcNAc-containing glycoproteins are selected for a single central nervous system disease in this embodiment, all of these glycoproteins can serve as index markers for the particular central nervous system disease. Such a plurality of index markers are advantageous because these index markers permit multidimensional diagnosis and can thus achieve more accurate diagnosis. Alternatively, even if one index marker is selected for a plurality of central nervous system diseases, the index marker is effective as long as the particular central nervous system disease can be distinguished from a different central nervous system disease similar in symptom thereto using the index marker. For example, as described later in Examples, the expression level of α2-macroglobulin increases in the spinal fluid of an NMO patient. In this context, the expression level of spinal fluid α2-macroglobulin may increase in a patient having a different central nervous system disease. Even in such a case, this α2-macroglobulin can serve as an effective index marker for NMO in the diagnosis of a patient as having either NMO or MS unless its expression level increases in the spinal fluid of a patient having MS very similar in symptom to NMO. Furthermore, one index marker may serve as an index marker for a plurality of central nervous system diseases that exhibit similar symptoms. Even in such a case, each disease can be identified by the combination pattern of the index marker with an index marker specific for the disease as long as each individual central nervous system disease has a plurality of different index markers. Thus, the index marker can still function.

Conventional techniques hardly even isolate a novel index marker for a particular central nervous system disease from a body fluid, etc. Even more, it has heretofore been nearly impossible to exhaustively isolate a plurality of index markers for a single central nervous system disease. The method of this embodiment can easily and exhaustively isolate index marker(s) for a particular central nervous system disease from, for example, the spinal fluid glycoproteins of Table 1 enriched or isolated from a body fluid, etc.

Embodiment 3: Kit for Enriching or Isolating Terminal GlcNAc-Containing Glycoprotein The third embodiment of the present invention relates to a kit that can selectively enrich or isolate a terminal GlcNAc-containing glycoprotein, i.e., a spinal fluid glycoprotein, from a body fluid, etc.

(Constitution)

The kit of this embodiment comprises a sialic acid-binding substance and a GlcNAc-binding substance as essential constituents.

Examples of the sialic acid-binding substance include an anti-sialic acid antibody and/or a sialic acid-binding lectin. The terminal sialic acid-containing glycoprotein targeted by this kit is preferably a glycoprotein having α2,6 sialic acid at a sugar chain terminus. Thus, the anti-sialic acid antibody included in this kit is preferably an anti-α2,6 sialic acid antibody or an active fragment thereof. The sialic acid-binding lectin can be α2,6 sialic acid-binding lectin. For example, 300177 from Seikagaku Biobusiness Corp. or J1001014 from Medical & Biological Laboratories Co., Ltd. (MBL) can be used as SSA lectin. L6890 Lectin from *Sambucus nigra* (elder) from Sigma-Aldrich Corp. can be used as SNA lectin. 300186 from Seikagaku Biobusiness Corp. can be used as TJA-I lectin.

The GlcNAc-binding substance is preferably, for example, an anti-GlcNAc antibody or an active fragment thereof. Examples of the anti-GlcNAc antibody include OMB4 antibody (Ozawa, H et. al., Archives of Biochemistry and Biophysics 1997, vol. 342 (1), p. 48-57). Alternatively, a GlcNAc-binding lectin can be used. For example, 165-17591 *Psathyrella Velutina* Lectin from Wako Pure Chemical Industries, Ltd. or Recombinant PVL from Medical & Biological Laboratories Co., Ltd. (MBL) can be used. 300191 from Seikagaku Biobusiness Corp. or J1001016 from Medical & Biological Laboratories Co., Ltd. (MBL) can be used as WGA lectin.

The kit of this embodiment can also comprise a buffer for complex dissociation, in addition to the constituents. The "buffer for complex dissociation" refers to a buffer having chaotropic effect capable of dissociating the complex of the terminal GlcNAc-containing glycoprotein and the GlcNAc-binding substance. The buffer for complex dissociation corresponds to, for example, a high-salt concentration (e.g., $Mg^{2+}>2$ M) buffer, a strongly acidic buffer (pH>2.5), or a buffer containing a chaotropic agent (e.g., GlcNAc).

The kit of this embodiment may further comprise an albumin-binding substance. Specific examples of the albumin-binding substance include Blue Sepharose, and an anti-albumin antibody and an active fragment thereof.

The sialic acid-binding substance, the GlcNAc-binding substance, and the optional albumin-binding substance may be immobilized on carriers or labeled with fluorescent dyes, luminescent substances, or the like, if necessary.

The kit of this embodiment can comprise, in addition to the constituents, columns (spin columns, etc.) to be packed with the sialic acid-binding substance, the GlcNAc-binding substance, and the optional albumin-binding substance, a buffer for washing (a PBS buffer, saline, etc.), and/or an instruction stating protocols, etc.

The kit of this embodiment may further comprise a substance binding to an index marker for a particular central nervous system disease. The "substance binding to an index marker for a particular central nervous system disease" refers to a substance that can specifically recognize a heretofore known index marker for a particular central nervous system disease or the index marker (terminal GlcNAc-containing glycoprotein) obtained by the method of Embodiment 2 or the like and bind thereto. The substance corresponds to, for example, an antibody against a particular terminal GlcNAc-containing glycoprotein, or an active fragment thereof. Specific examples thereof include antibodies (anti-transferrin-1 antibody and anti-transferrin-2 antibody) against transferrin-1 and transferrin-2 (Patent Literature 3), which are index markers for idiopathic normal pressure hydrocephalus (iNPH), and active fragments thereof.

The kit of this embodiment further comprising such a substance binding to an index marker for a particular central nervous system disease can serve as a kit for diagnosis of the particular central nervous system disease. Specifically, an index marker associated with the particular disease (iNPH in the example described above) in the terminal GlcNAc-containing glycoprotein group in a body fluid collected from a test subject can be detected or quantified using the substance binding to the index marker for the disease supplied with the kit. When the quantification results exhibit a statistically significant quantitative difference from those of the control subject, the test subject can be diagnosed as having, with high probability, the central nervous system disease corresponding to the substance binding to the index marker for the disease.

(Effect)

The kit of this embodiment can conveniently and efficiently isolate or enrich a terminal GlcNAc-containing glycoprotein, i.e., a spinal fluid glycoprotein, from a body fluid, etc.

Embodiment 4: Index Marker for Central Nervous System Disease

The fourth embodiment of the present invention relates to an index marker for central nervous system disease.

The "index marker for central nervous system disease" of this embodiment is based on one or more glycoprotein(s) selected from the glycoprotein group of Table 1 obtained using the method of Embodiment 2 in Example 2 described later, or fragments(s) thereof.

All of the 13 glycoproteins set forth in Table 1 are the spinal fluid glycoproteins according to the present invention, i.e., glycoproteins each containing a GlcNAc residue at a non-reducing terminus and having an α2,6 sialic acid-free sugar chain. The "fragment thereof" is a fragment of each glycoprotein set forth in Table 1 and refers to a glycoprotein fragment that contains a GlcNAc residue and has an α2,6 sialic acid-free sugar chain.

Specific examples of the "index marker for central nervous system disease" of this embodiment include α2-macroglobulin shown in Table 1 or a fragment thereof for neuromyelitis optica (NMO) as the central nervous system disease. As described in Embodiment 2, α2-macroglobulin containing a GlcNAc residue and having an α2,6 sialic acid-free sugar chain or a fragment thereof increases in an NMO patient but does not increase in an MS patient (see Example 3 described later). Thus, the α2-macroglobulin or the fragment thereof can serve as a very useful index marker for NMO or MS in the diagnosis of a test subject as having either NMO or multiple sclerosis (MS).

Embodiment 5: Method for Determining Developed Central Nervous System Disease (Summary and Constitution)

The fifth embodiment of the present invention relates to a method for determining the presence or absence of a particular central nervous system disease developed. The method of this embodiment comprises a central nervous system disease index marker detection step and a development determination step.

5-1. Central Nervous System Disease Index Marker Detection Step.

The "central nervous system disease index marker detection step" refers to the step of detecting the index marker for central nervous system disease of Embodiment 4 from a body fluid or a central neural cell derived from a test subject.

The index marker for central nervous system disease is preferably detected from a body fluid or a central neural cell derived from a test subject by a method involving enriching or isolating the index marker for central nervous system disease, i.e., the spinal fluid glycoprotein, or a fragment thereof contained in the body fluid or the central neural cell using the method for enriching or isolating a terminal GlcNAc-containing glycoprotein according to Embodiment 1.

The types and number of index markers for central nervous system disease of Embodiment 4, i.e., glycoproteins in the glycoprotein group set forth in Table 1, or fragments thereof to be detected from the body fluid or the central neural cell derived from a test subject can be determined appropriately according to the type of a particular central nervous system disease whose presence or absence of development is to be determined, and a purpose. In this context, the "purpose" includes, for example: the determination of whether a test subject is affected with a certain central nervous system disease or is healthy as in physical checkup, i.e., the determination of the presence or absence of a particular central nervous system disease on condition that no central nervous system disease has been identified; or the final determination of a difficult-to-diagnose central nervous system disease already developed in a test subject in the case where the disease has been narrowed down to some candidates based on its symptoms but cannot be diagnosed definitely due to very similar symptoms among the candidate diseases. Specific examples of the case intended for the latter purpose include the final determination of a test subject as having either NMO or multiple sclerosis (MS). In this case, only α2-macroglobulin shown in Table 1 or a fragment thereof suffices as the index marker for central nervous system disease to be detected.

A method for detecting the index marker for central nervous system disease is not particularly limited. Any method known in the art can be used as long as the method can detect the index marker for central nervous system disease of interest. If a target molecule has already been identified, antigen-antibody reaction method, particularly, sandwich ELISA, can be used preferably.

JP Patent Publication (Kokai) No. 2010-121980 A (2010) (Patent Literature 2) utilized Western blotting or lectin blotting for the quantification of spinal fluid transferrin. More preferably, high-throughput sandwich ELISA, which is superior in assay sensitivity or quantitative performance to blotting, can be used.

JP Patent Publication (Kokai) No. 2010-121980 A (2010) (Patent Literature 2) describes a (antibody/lectin) sandwich ELISA method comprising adsorbing an anti transferrin antibody (capturing antibody) onto a plate, and detecting the sugar chain moiety of captured spinal fluid transferrin using PVL lectin. It has however been shown to be difficult to achieve quantitative assay by this method, presumably due to the weak binding of PVL lectin. By contrast, the method developed in the present invention involves adsorbing PVL lectin onto a plate, capturing all spinal fluid molecules having sugar chains, and then detecting the molecule of interest using an antibody against the molecule (lectin/antibody sandwich ELISA). This method produced a favorable value of 80% to 90% in the additional recovery experiment of spinal fluid transferrin. In addition, the preparation of only one PVL lectin plate according to the present invention permits simultaneous quantification of arbitrary or all molecules of the 13 spinal fluid glycoproteins. The paper of Matsuda et al. (Matsuda, et al., Hepatology, 2010 July; 52 (1): 174-82) has already showed that lectin/antibody sandwich ELISA, which is a technique known in the art, is useful in the assay of mucin carbohydrate antigens. In the present invention, plural types of spinal fluid marker molecules (probably derived from the central nervous system) having sugar chains can be assayed at the same time. As a result, not only can the sensitivity and specificity of diagnosis be enhanced, but also a particular disease can be distinguished from many types of diseases.

5-2. Determination Step.

The "development determination step" refers to the step of determining whether or not the test subject is affected with a particular central nervous system disease.

This step is the step of finally determining whether or not the test subject is affected with a particular central nervous system disease on the basis of the detection results obtained in the central nervous system disease index marker detection step. As described in Embodiment 2, the index marker for central nervous system disease used in this embodiment has the predetermined pattern of detection of the particular central nervous system disease (i.e., increase or decrease in its content). Referring to the example mentioned above, α2-macroglobulin used as the index marker for central nervous system disease in the case of NMO as the particular central nervous system disease increases in an NMO patient, whereas α2-macroglobulin in the case of MS as the particular central nervous system disease does not increase in an MS patient. Thus, when a test subject is presumed to have either NMO or MS from his or her symptoms, use of α2-macroglobulin as the index marker for central nervous system disease can determine the presence of NMO developed in the test subject with increase in the content of the marker or can determine the presence of MS developed in the test subject with no detectable content of the marker. Since these diseases differ in treatment method, this distinction is important.

The pattern of detection of a particular central nervous system disease using each glycoprotein set forth in Table 1 or a fragment thereof may be stored in a database. In such a case, the minimum necessary index markers for central nervous system disease to be detected can be selected immediately for determining the presence or absence of various central nervous system diseases developed. Thus, this approach is convenient.

Example 1

Enrichment of Spinal Fluid Glycoprotein
(1) Enrichment of Spinal Fluid Glycoprotein Using Isolation or Enrichment Method of the Present Invention.

Spinal fluid glycoproteins were isolated using the method for enriching or isolating a terminal GlcNAc-containing glycoprotein according to Embodiment 1 of the present invention.

First, test subject-derived spinal fluid (11 mL, 0.47 mg/mL) was dialyzed against a phosphate buffer (20 mM, pH 7.0) for desalting prior to chromatography. The obtained dialysate was applied to a Blue Sepharose column (HiTrap Blue HP; GE Healthcare) (5 mL) for albumin removal. A nonbinding fraction (fraction A) eluted from the column, i.e., a fraction from which albumin was removed, was recovered (albumin removal step). This fraction A is rich in serum glycoproteins having α2,6-sialic acid. Thus, in order to remove these serum glycoproteins, 20 mL of fraction A was subsequently applied to an SSA lectin column (Seikagaku Corp.) (5 mL) specifically binding to α2,6-sialic acid (terminal sialic acid-containing glycoprotein removal step). Spinal fluid glycoproteins each have GlcNAc at a sugar chain terminus and as such, are eluted as a nonbinding fraction (fraction B) without being adsorbed on the SSA lectin column. This fraction B can be recovered so that serum glycoproteins present in the spinal fluid can be removed while spinal fluid glycoproteins can be concentrated selectively.

Subsequently, 30 mL of fraction B thus recovered after SSA lectin column chromatography was applied to a PVL lectin column (Wako Pure Chemical Industries, Ltd.) (5 mL) specifically binding to GlcNAc. As a result, terminal GlcNAc-containing glycoproteins (spinal fluid glycoproteins) in fraction B bind to the PVL lectin column (terminal GlcNAc-containing glycoprotein complex isolation step). In this context, a nonbinding fraction eluted from the column was designated as fraction C. The column was washed five times with 4 mL of PBS, followed by the specific elution of the bound spinal fluid glycoproteins with 0.2 M GlcNAc (Sigma-Aldrich Corp.) to recover a terminal GlcNAc-containing glycoprotein-enriched fraction (fraction D: PVL column eluted fraction).

(2) Confirmation of Serum Glycoprotein in Each Fraction.

The fraction obtained in each step in the paragraph (1) was examined for the presence or absence of serum glycoproteins.

Human spinal fluid and the fractions B to D each corresponding to 20 µg of proteins were separately mixed with Laemmli sample buffer, heated, and then subjected to SDS/PAGE using 4 to 20%-gradient polyacrylamide gels. Transferrin-2 and transferrin-1 were used as indexes for serum glycoproteins and spinal fluid glycoproteins, respectively. Electrophoresis was conducted at a constant current of 40 mA for 55 minutes.

Subsequently, for SSA lectin blotting, each sample was electrically transferred to a PVDF membrane at a constant current of 260 mA for 50 minutes. The membrane was blocked with a PBS buffer containing 1% BSA for 1 hour or longer. Then, the PVDF membrane thus blotted was reacted for 1 hour with biotinylated SSA lectin diluted with 1% BSA-PBS. Subsequently, the PVDF membrane was washed three times each for 15 minutes with a PBS washing solution containing 0.05% Tween 20.

The membrane thus washed was reacted for 1 hour with a streptavidin-horseradish peroxidase conjugate HRP (Amersham, #RPN1231V) diluted with 1% BSA-PBS. Then, the membrane was washed three times each for 15 minutes with the washing solution. Subsequently, the bands of glycoproteins were detected using a chemiluminescent substrate (Pierce SuperSignal West Dura Extended Duration Substrate) and Lumino Image Analyzer (LAS-1000 plus; Fujifilm Corp.). In this experiment, biotin-SSA (Seikagaku Corp. #300442) was used at a concentration of 1 µg/mL. Since biotinylated PVL is not commercially available, unlabeled PVL lectin (Wako Pure Chemical Industries, Ltd., Cat. No. 165-17591) was purchased and biotinylated in the presence of 10 mM GlcNAc. The biotinylating agent used was Ez-Link NHS-Biotin (Thermo Fisher Scientific Inc. (Pierce), Cat. No. 21336). The 10 mM GlcNAc was used for preventing the binding site of sugar from being inactivated by biotinylation through its interaction with the biotinylating agent.

(Results)

Figure 3:
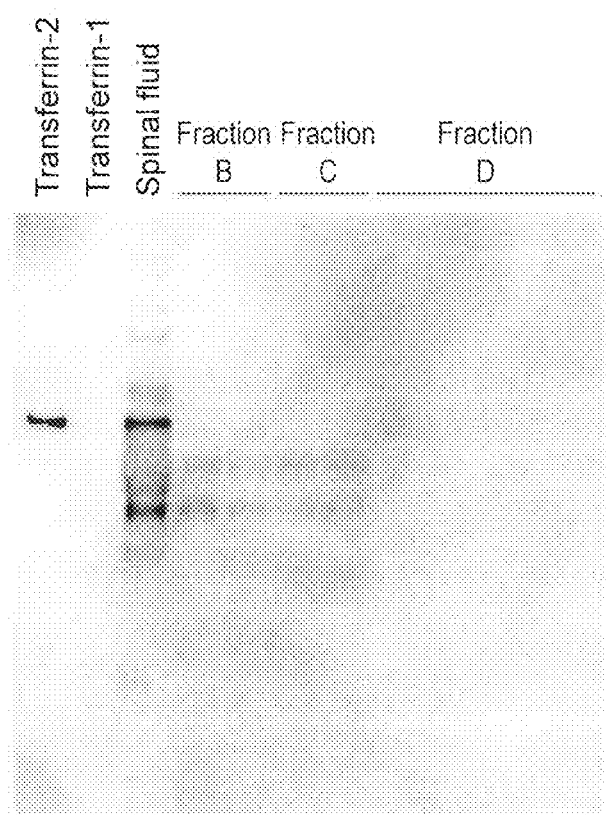
FIG. 3 shows results of SSA lectin blotting showing the presence or absence of a serum glycoprotein transferrin-2 (TF-2) in a fraction obtained in each step of the method of the first embodiment of the present invention, wherein the glycoprotein was detected using an anti-transferrin antibody. SSA lectin-reactive TF-2 was not detected in fraction D (enriched fraction), which was an eluted fraction from a PVL column.

The results are shown in FIG. 3. The bands detected in this experiment are derived from blood glycoproteins. As also described in Background Art in the present specification, spinal fluid has been confirmed to contain a large number of serum proteins, i.e., blood glycoproteins. Many bands of blood glycoproteins in spinal fluid disappeared in fraction B eluted from the SSA lectin column, demonstrating that the majority of blood glycoproteins were removed by the terminal sialic acid-containing glycoprotein removal step. Blood glycoprotein-derived bands were still slightly observed in fraction B but completely disappeared in fraction D eluted after adsorption on the PVL lectin column. By contrast, bands derived from blood glycoproteins in almost the same amount as in fraction B were observed in fraction C eluted from the PVL lectin column. This result demonstrated that the terminal GlcNAc-containing glycoprotein complex isolation step using an SSA lectin column can almost completely remove residual blood glycoproteins in fraction B. The results described above showed that the method for enriching and isolating a spinal fluid glycoprotein according to the present invention can selectively remove blood glycoproteins in a body fluid.

(3) Confirmation of Spinal Fluid Glycoprotein in Each Fraction.

Unlike the preceding experiment, whether or not spinal fluid glycoproteins were enriched by the method of the present invention was in turn examined.

(Methodology)

Laemmli sample buffer was added to human spinal fluid and the fractions B and D each corresponding to 0.04 μg of proteins, and the mixtures were heated and then subjected to SDS/PAGE using 4 to 20%-gradient polyacrylamide gels. Transferrin-2 and transferrin-1 were used as indexes for serum glycoproteins and spinal fluid glycoproteins, respectively, as in the paragraph (2). Electrophoresis was conducted at a constant current of 40 mA for 55 minutes.

The isolated proteins of each sample were electrically transferred to a PVDF membrane at a constant current of 260 mA for 50 minutes by a blotting method known in the art. After the transfer, the membrane was blocked with tris-buffered saline (TBS) containing 5% skimmed milk and 0.1% Tween 20 for 1 hour or longer.

Next, an antibody (1 to 2 μg/mL) diluted 1:1000 with TBS containing 3% skimmed milk was added to the membrane and reacted for 1 hour. The membrane was washed three times each for 15 minutes with a TBS washing solution containing 0.1% Tween 20.

Subsequently, the membrane was reacted for 1 hour with Anti-Rabbit IgG, Horseradish Peroxidase (Amersham, #NA934V) (1 μg/mL) diluted 1:1000 with TBS containing 3% skimmed milk. Again, the membrane was washed three times each for 15 minutes with the washing solution. The bands of glycoproteins were detected using a chemiluminescent substrate (Pierce SuperSignal West Dura Extended Duration Substrate) and Lumino Image Analyzer (LAS-1000 plus; Fujifilm Corp.). An anti-human transferrin antibody (Bethyl Laboratories, Inc., Cat. No. A80-128A, Lot No. A80-128A-5) was used in the Western blotting of transferrin.

(Results)

Figure 4:
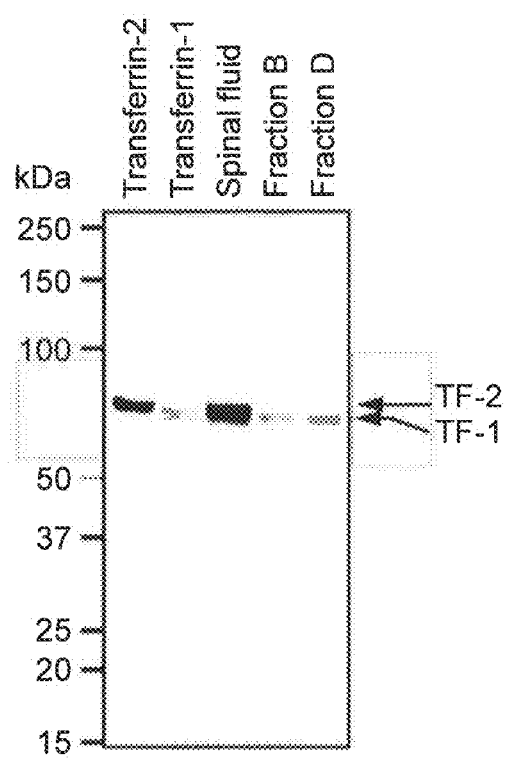
FIG. 4 shows results of Western blotting showing the state of enrichment of a spinal fluid glycoprotein in a fraction obtained in each step of the method of the first embodiment of the present invention. Only a band of the same mobility as in transferrin-1 (TF-1) was detected in fraction D (enriched fraction), which was an eluted fraction from a PVL column.

The results are shown in FIG. 4. These results demonstrated that, of transferrins present in unpurified spinal fluid, only the spinal fluid glycoprotein transferrin-1 was selectively present in fractions B and D and found in a more concentrated level in fraction D than in fraction B. Thus, the method for enriching and isolating a spinal fluid glycoprotein according to the present invention was shown to be capable of selectively concentrate and recover spinal fluid proteins in a body fluid.

The results of the paragraphs (2) and (3) together demonstrated that the method for enriching and isolating a spinal fluid glycoprotein according to the present invention can remove blood glycoproteins in a body fluid and selectively enrich and isolate spinal fluid glycoproteins.

(4) Sugar Chain Profiling Using Lectin Microarray.

The enrichment of spinal fluid glycoproteins by the method of the present invention was confirmed using a lectin microarray.

(Methodology)

The confirmatory experiment shown below requires desalting and concentrating beforehand each solution after fractionation of the paragraph (1). Thus, each fraction solution was concentrated using 2-D Clean-Up kit (GE Healthcare Japan Corp.). The obtained precipitate was redissolved in 20 μL of a PBS buffer.

The sugar chain profiling of glycoproteins in unpurified spinal fluid and an enriched fraction using a lectin microarray was basically conducted according to the method described in Kuno, A. et al., Nature Methods. 2, 851-856 (2005), and Uchiyama N., Proteomics 8, 3042-3050 (2008). Unpurified spinal fluid (0.47 mg/l) and a concentrate of fraction D (1.42 mg/mL) were diluted 10-fold with PBS buffers. These samples (4.3 μL and 1.4 μL, respectively) each corresponding to 200 ng in terms of the amount of proteins were adjusted to 10 μL with PBS buffers containing 1% Triton X-100. To each solution, 20 μg of a fluorescent labeling reagent (Cy3-SE, GE Healthcare Japan Corp.) was added and reacted at morn temperature for 1 hour to complete fluorescent labeling. To the reaction product, 90 μL of a glycine-containing buffer solution was added and reacted at room temperature for 2 hours to inactivate a redundant fluorescent labeling reagent. This fluorescently labeled glycoprotein solution was applied to a lectin microarray. The lectin microarray used was an array on which 43 different lectins were immobilized. In order to optimize obtained binding signals for subsequent comparative analysis, each sample was prepared into four dilution series, which were then applied to the lectin microarray. The binding reaction between the lectins and the analyte glycoproteins was performed at 20° C. for 12 hours. After the reaction, the sample solution on the array was removed, and the array was washed three times with a special buffer and then scanned using a lectin microarray scanner GlycoStation™ Reader 1200 manufactured by GP Biosciences Ltd. The data obtained by scanning was stored in jpeg and TIFF files. Image diagrams were drawn using the jpeg file.

(Results)

Figure 5:
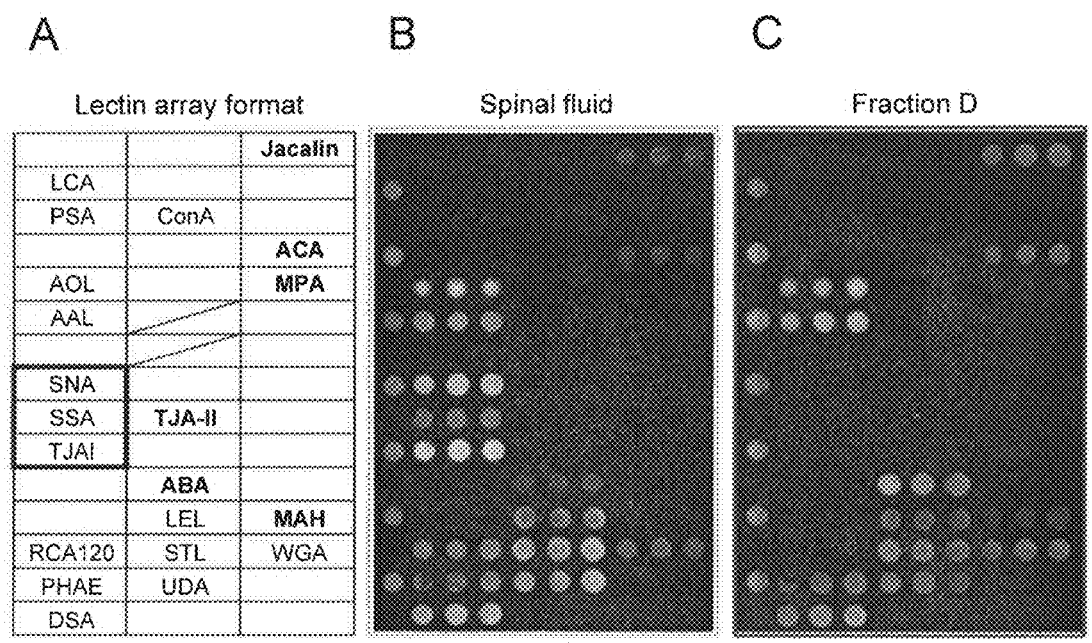
FIG. 5 is a diagram showing profiling using a lectin microarray.

The results are shown in FIG. 5. From both the samples of unpurified spinal fluid and serum, strong signals were observed for SSA, SNA, and TJA-I lectins. These lectins each bind to α2,6 sialic acid, which is a sugar in the sugar chain of a blood glycoprotein. Thus, the majority of glycoproteins contained in spinal fluid were shown to have terminal α2,6 sialic acid typical of blood glycoproteins. By contrast, signals derived from α2,6 sialic acid-binding lectins were hardly detected in fraction D enriched by the method of the present invention. Instead, strong signals were exhibited for WGA and ABA lectins. These lectins each bind to GlcNAc at a sugar chain terminus. Also, the presence of bisecting β-1,4-GlcNAc was indicated by signals derived from PHAE and UDA, while the presence of core fucose was indicated by signals derived from PSA, LCA, and AAL. All of these sugars are characteristic of the sugar chains of spinal fluid glycoproteins. Signals derived from Jacalin, ACA, and MAH also increased after enrichment, indicating enhanced abundances of sugar chains binding thereto. This means that the glycoproteins enriched using PVL lectin include glycoproteins containing not only N-linked sugar chains but O-linked sugar chains. The results described above showed that glycoproteins having terminal α2,6 sialic acid are efficiently removed from fraction D obtained by the enrichment or isolation method of the present invention, while only spinal fluid glycoproteins having terminal GlcNAc are concentrated therein.

(5) Analysis by Mass Spectrometry

The enrichment of spinal fluid glycoproteins by the method of the present invention was confirmed by mass spectrometry.

(Methodology)

As described in the paragraph (4), each solution after fractionation of the paragraph (1) was desalted and concentrated beforehand. An unpurified spinal fluid sample (150 μL) and fraction D (50 μL) were each precipitated with acetone. Each obtained precipitate was reduced at room temperature for 1 hour by the addition of 50 μL of Milli-Q Water, 50 μL of a 7 M guanidine-HCl/0.5 M Tris-HCl (pH 8.6)/10 mM EDTA-Na solution, 20 μL of a 1 M Tris-HCl (pH 8.6) solution, and 10 μL of a 100 mM 1,4-dithio-DL-threitol (Wako Pure Chemical Industries, Ltd.) solution, and then alkylated at room temperature for 1 hour in the dark by the addition of 10 μL of a 200 mM 2-iodoacetamide (Wako Pure Chemical Industries, Ltd.) solution. The reaction product was dialyzed (8 kDa cut off) at 4° C. using 5 L of a 10 mM ammonium bicarbonate solution as an external solution and then freeze-dried. To this sample, a trypsin solution (2 μg of trypsin dissolved in 50 μL of a 50 mM ammonium bicarbonate solution) was added, and the mixture was incubated overnight at 37° C. and then heated at 100° C. for 5 minutes. After standing to cool to room temperature, 10 μL of a 5 mU PNGase F (TaKaRa Bio Inc.) solution was added to the reaction solution, and the mixture was incubated overnight at 37° C. To this reaction solution, 5 μL of a 50% acetic acid solution was added, and the mixture was incubated at 37° C. for 30 minutes, then deproteinized using a simplified column Oasis HLB (10 mg/mL, Waters Corp.), and then concentrated under reduced pressure to purify N-linked sugar chains from each of the spinal fluid sample and the fraction D.

Next, to the obtained N-linked sugar chains, 40 μL of a reducing solution (500 mM sodium borohydride/50 mM sodium hydroxide solution) was added, and the mixture was incubated overnight at 45° C. Then, 5 μL of a 50% acetic acid solution was added thereto on ice to decompose an excessive reagent. After desalting and concentration under reduced pressure using a cationic resin (AG50W-X8(H+), Bio-Rad Laboratories, Inc.), the concentrate was subjected to azeotropy with a methanol solution containing 1% acetic acid to remove the residual reagent.

The obtained sample was transferred to a glass vial and dried. Approximately 50 mg of sodium hydroxide (Fluka) was ground using 250 μL of dimethyl sulfoxide (Wako Pure Chemical Industries, Ltd.) in a mortar, and 50 μL of the obtained sodium hydroxide suspension was added to the dried sample and mildly mixed. Then, 50 μL of methyl iodide (Wako Pure Chemical Industries, Ltd.) was added thereto and reacted for 30 minutes in a shaker. Next, the reaction solution was neutralized by the addition of 150 μL of a 50% acetic acid solution on ice. Then, 850 μL of distilled water was further added thereto, and the resulting solution was purified by application to a simplified column Sep-Pak C18 (50 mg/mL, Waters Corp.). Fractions were eluted with 600 μL of acetonitrile and then concentrated under reduced pressure. 0.5 μL of a matrix solution (10 mg of 2,5-dihydroxybenzoic acid dissolved in 1 mL of 30% ethanol) was applied to a stainless MALDI plate. Subsequently, each completely methylated sample was redissolved in 25 μL of acetonitrile, and 0.5 μL of the solution was applied to the plate, mixed therewith on the plate, and dried in air, followed by MS analysis. All runs of the MS analysis were conducted on a positive ion mode. For MS profiles, three measurements were conducted for each sample using MALDI-TOF MS (Reflex IV, Bruker-Daltonics K.K.), and an average of the results of these three measurements was indicated in a graph form for the monoisotopic peak relative intensity of the obtained MS signal (with total intensity as 100). Sugar chain structures were determined using MALDI-QIT-TOF MS (AXIMA-QIT, Shimadzu Corp.).

(Results)

Figure 6:
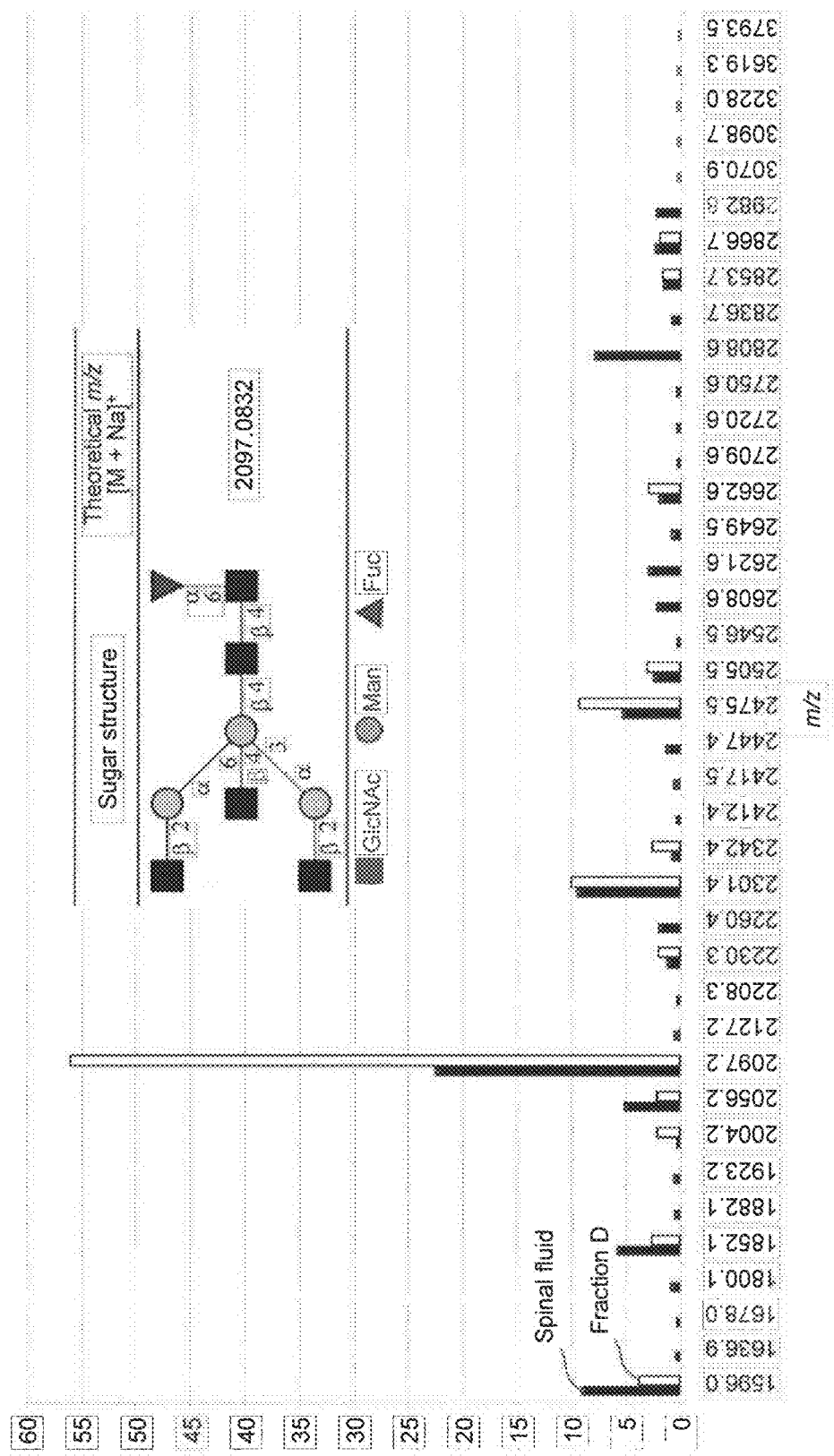
FIG. 6 is a diagram showing mass spectrometry results of spinal fluid and fraction D (enriched fraction), which was an eluted fraction from a PVL column.

The results are shown in FIG. 6. As a result of analysis by mass spectrometer, methylated sugars obtained from glycoproteins contained in spinal fluid exhibited a major peak of m/z=2097.2. This peak agrees with structures having biantennary asialo-agalacto-complex N-glycans, i.e., bisecting β1,4-GlcNAc and core α1,6-fucose (sugar chains of spinal fluid glycoproteins), showing that most of these sugar chains are derived from IgG most abundantly contained as serum glycoproteins. In addition, the peaks of various sugar chains found in serum also appeared. This supported the finding that the majority of glycoproteins in spinal fluid are derived from serum.

For methylated sugars derived from the fraction eluted from the PVL lectin column (fraction D), the ratio of the peak of m/z=2097.2 that agrees with the sugar chains of spinal fluid glycoproteins increased by approximately 2.5 times compared with the spinal fluid and accounted for 55% of all peaks. This result means that sugar chains corresponding to the peak of m/z=2097.2 were efficiently enriched. Thus, these mass spectrometry results also demonstrated that the enrichment or isolation method of the present invention removed serum glycoproteins and enriched spinal fluid glycoproteins.

Example 2

Identification of Spinal Fluid Glycoprotein Using Mass Spectrometer.

The spinal fluid glycoprotein group obtained by the enrichment or isolation method of the present invention was identified using a mass spectrometer.

(Methodology)

The concentrated fraction D (enriched fraction) obtained in Example 1 was dissolved in a sample buffer for electrophoresis, reacted at 100° C. for 5 minutes, and separably developed on a 5 to 20%-gradient gel. The developed gel was stained with silver according to a protocol for mass spectrometry shown below. The composition of the solutions used is as follows:

Fixing solution (50% methanol (Sigma-Aldrich Corp.) and 5% acetic acid (Wako Pure Chemical Industries, Ltd.))

Washing solution (50% methanol)

Sensitizing solution (0.02% sodium thiosulfate (Wako Pure Chemical Industries, Ltd.))

Silver nitrate solution (0.1% silver nitrate (Sigma-Aldrich Corp.))

Developing solution (0.04% formaldehyde (Wako Pure Chemical Industries, Ltd.) and 2% sodium carbonate (Wako Pure Chemical Industries, Ltd.))

Stopping solution (5% acetic acid)

The gel was shaken for 20 minutes in the fixing solution, subsequently for 10 minutes in the washing solution, and further for 10 minutes in pure water. Next, the gel was reacted for 1 minute in the sensitizing solution and then shaken for 1 minute in pure water. After subsequent replacement by the silver nitrate solution, the gel was shaken therein at a low temperature for 20 minutes, then shaken for 1 minute in pure water, and placed in the developing solution. Color emitted therefrom was confirmed, and the developing solution was replaced by the stopping solution. The resulting gel was stored. After cleavage of bands of the analytes, in-gel digestion was carried out. Proteins in the sample were identified by analysis using a mass spectrometer. After the cleavage of bands of the analyte proteins, the stained gel was decolorized according to procedures shown below. The composition of the solutions used is as follows:

30 mM potassium ferricyanide (Wake Pure Chemical Industries, Ltd.)
100 mM sodium thiosulfate These stock solutions were mixed at a 1:1 ratio, and 50 μL of the mixture per band was added thereto and reacted for 5 minutes. Subsequently, the reaction product was shaken for 5 minutes in pure water.

Subsequently, procedures from reductive alkylation to enzymatic digestion reaction and peptide extraction were performed as shown below. In this context, the composition of the solutions used is as follows:

Reducing solution (10 mM DTT (Wako Pure Chemical Industries, Ltd.) and 25 mM ammonium bicarbonate (Wake Pure Chemical Industries, Ltd.))

Buffer for washing (25 mM ammonium bicarbonate)

Alkylating solution (55 mM iodoacetamide (Wake Pure Chemical Industries, Ltd.) and 25 mM ammonium bicarbonate)

Dehydrating solution (50% acetonitrile (Wako Pure Chemical Industries, Ltd.) and 50 mM ammonium bicarbonate)

Enzyme trypsin solution (10 μg/mL trypsin (Promega Corp.) and 50 mM ammonium bicarbonate)

Extracting solution (50% acetonitrile and 5% trifluoroacetic acid (Wako Pure Chemical industries, Ltd.))

The decolorized gel was shaken for 5 minutes in the dehydrating solution, which was then replaced by 100 μL of the reducing solution, followed by shaking at 56° C. for 1 hour. After standing to cool to room temperature, the gel was shaken for 10 minutes in the buffer for washing, which was then replaced by 100 μL of the alkylating solution, followed by shaking at room temperature for 45 minutes in the dark. The gel was shaken for 10 minutes in the buffer for washing and for 10 minutes in the dehydrating solution. Then, the enzyme trypsin solution was added thereto and reacted overnight at 37° C. 50 μL of the extracting solution per sample was added thereto, and the mixture was shaken at room temperature for 30 minutes, followed by recovery of the extract. 25 μL of the extracting solution was further added thereto, and the mixture was shaken for 30 minutes. The solutions of these two extractions were combined and vacuum-concentrated under reduced pressure. This sample solution was used in analysis using a mass spectrometer.

For analysis by MALDI-TOF mass spectrometry, the sample solution was desalted and concentrated using Zip-Tip-C18 (Millipore Corp.). The obtained concentrate was mixed with CHCA (alpha-cyano-4-hydroxycinnamic acid Bruker-Daltonics K.K.)). Peptide masses were measured by analysis using a MALDI-TOF mass spectrometer (Ultraflex III, Bruker-Daltonics K.K.). Proteins were identified using MS-Fit in ProteinProspector, the program package developed by UCSF.

(Results)

The SDS-PAGE analysis of proteins present in fraction D (enriched fraction) showed the presence of 20 or more types of spinal fluid glycoproteins. Of them, 13 glycoproteins are shown in Table 1 above. A glycoprotein having the largest content was transferrin 1, which was identified by the present inventors in Patent Literature 3. Also, prostaglandin D2 synthase known as a spinal fluid glycoprotein was contained in the fraction. Thus, the method of the present invention was shown to selectively enrich spinal fluid glycoproteins. The results described above demonstrated that the method of the present invention can easily and exhaustively enrich or isolate spinal fluid glycoproteins, which have heretofore been difficult to even detect. The isolation conditions (e.g., the type of lectin) or the quantification conditions can be changed to thereby presumably isolate a larger number of different spinal fluid glycoproteins. The spinal fluid glycoproteins thus isolated can become index marker candidates for various central nervous system diseases.

Example 3

Search for Index Marker for Central Nervous System Disease in Enriched Fraction.

Multiple sclerosis (MS) is a demyelinating disease of central nerves and is thought to occur due to autoimmunity. Neuromyelitis optica (NMO) had historically been regarded as a subtype of MS complicated by optic neuritis. In 2005, however, an anti-aquaporin 4 antibody was shown to be positive in the serum of many NMO patients, suggesting that NMO is an independent disease different from MS. On the other hand, the anti-aquaporin 4 antibody is negative in some NMO patients. In the case of the latter NMO patients negative for the anti-aquaporin 4 antibody, it has been exceedingly difficult to diagnose the patients as having either NMO or MS by conventional methods. Thus, an index marker for central nervous system disease was searched for which permits accurate diagnosis of NMO in patients including such anti-aquaporin 4 antibody negative patients.

(Methodology)

The spinal fluid glycoproteins of Table 1 as index marker candidates for central nervous system disease that were enriched by the method of Embodiment 1 and identified in Example 2 were searched by Western blotting for a glycoprotein differing between an NMO patient and a control subject MS patient, i.e., a possible NMO index marker with respect to MS, provided that antibodies against the glycoproteins were available.

First, spinal fluid glycoproteins were enriched from the respective spinal fluids of the NMO patient and the control subject according to the method of Example 1(1). Subsequently, Western blotting was performed using antibodies against various spinal fluid glycoproteins shown in Table 1 according to the method of Example 1(3). α2-macroglobulin, for which an antibody was easily available, was examined first as an NMO index marker candidate spinal fluid glycoprotein. The antibody used was an anti-human α2-macroglobulin antibody (ICN Biomedicals Inc., Cat. No. 55113) (1 to 2 μg/mL).

(Results)

Figure 7:
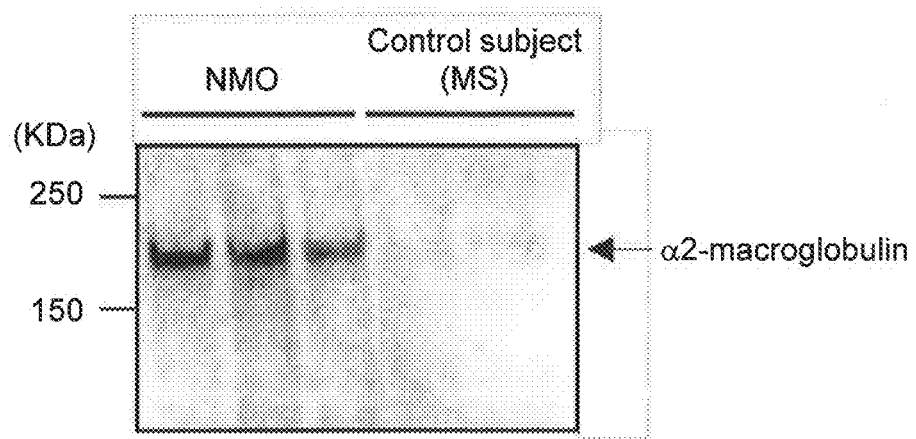
FIG. 7 is a diagram showing results of Western blotting by which the expression levels of α2-macroglobulins enriched from the respective spinal fluids of a neuromyelitis optica (NMO)-affected individual and a control subject (multiple sclerosis (MS)-affected/NMO-unaffected individual) were detected using an anti-α2-macroglobulin antibody.

The results are shown in FIG. 7. FIG. 7 shows α-macroglobulin in each enriched spinal fluid sample. The α2-macroglobulin was confirmed to obviously differ in expression level between the NMO patient and the control subject, i.e., the NMO-unaffected MS patient. Similar results were obtained even using anti-human α2-macroglobulin antibodies from other companies (e.g., Abcam plc., Cat. No. ab84176; Santa Cruz Biotechnology, Inc., Cat. No. sc-8514; and Dako Japan Inc., Cat. No. Q0102). The α2-macroglobulin was hardly detected in the MS patient, demonstrating that spinal fluid α2-macroglobulin having a sugar chain serves as an NMO index marker with respect to MS. For NMO, a drug with strong adverse reaction, such as asteroid drug, is used as a therapeutic drug. Thus, use of this marker as an index for determining drug efficacy offers a guideline for adverse reaction-free short-term treatment. Since the α2-macroglobulin has protease inhibitory activity, its expression seems to increase to prevent the inflammatory lesion of NMO from being spread.

Example 4

Search for Index Marker for Central Nervous System Disease in Unenriched Fraction.

Example 3 employed a sample containing spinal fluid glycoproteins enriched from the spinal fluid of a control subject or a patient according to the method of Example 1(1). Depending on the type of central nervous system disease, the amount of a spinal fluid glycoprotein in a body fluid may be much higher than that in a control subject. In such a case, use of the spinal fluid glycoprotein as an index marker for central nervous system disease is advantageous because central nervous system disease can be diagnosed rapidly and conveniently from a collected body fluid without enrichment treatment.

Thus, the spinal fluid glycoproteins of Table 1 identified in Example 2 were searched for an index marker for central nervous system disease capable of distinguishing two diseases that were difficult to distinguish due to their similar pathological conditions, as in NMO and MS.

(Methodology)

(1) Search for Index Marker for Central Nervous System Disease for Distinguishing Acute Disseminated Encephalomyelitis or Guillain-Barre Syndrome The "acute disseminated encephalomyelitis" (hereinafter, referred to as "ADEM") is an acute inflammatory demyelinating disease that is caused after viral infection or vaccination. This disease takes a monophasic course in most patients and, unlike MS, hardly recurs. ADEM is characterized by, for example, symmetrical lesions, strong inflammatory symptoms such as fever or meningeal irritation signs compared with MS, and highly frequent disturbance of consciousness or convulsion. ADEM, however, is very similar in lesion site itself to MS and thus, is exceedingly difficult to distinguish from the acute-stage symptoms of MS at the time of the earliest onset. Hence, the development of a diagnostic marker capable of definitely distinguishing ADEM from MS has been demanded.

Guillain-Barre syndrome is a disease that is caused by an autoantibody against nerves. Its symptoms involve the damages of motor nerves and also sensory nerves. Its pharyngeal-cervical-brachial variant is also known to damage cranial nerves. It is therefore important to distinguish the disease from multiple neuritis. The "multiple neuritis" is a disease that damages peripheral nerves in limbs due to drug addition, metabolic disorder, inherited disease, or the like. Numbness occurs in the peripheral portions of limbs in most patients, followed by motility disorder such as difficulty in walking.

Since the "Guillain-Barre syndrome" is an autoimmune disease, steroid therapy had been considered effective. In recent years, however, clinical trials have hardly showed its efficacy in both oral administration and intravenous therapy. Rather, steroid is used only on more rare occasions due to its potential risk of aggravating symptoms. Instead, plasma exchange therapy or large-volume injection (intravenous drip) of gamma globulin is currently conducted. Although this disease exhibits grave sequela in approximately 20% of patients, the frequency or degree of complications can be reduced by early treatment. Accordingly, early diagnosis is important.

Thus, the spinal fluid glycoproteins of Table 1 as index marker candidates for central nervous system disease identified in Example 2 were searched for an index marker for central nervous system disease that permitted differential diagnosis between MS and ADEM or between Guillain-Barre syndrome and multiple neuritis.

Specifically, first, spinal fluids were collected by lumbar puncture according to a standard method from an ADEM patient, a Guillain-Barre syndrome patient, and an individual having no central nervous system disease (ADEM-unaffected and Guillain-Barre syndrome-unaffected patient) as a control subject. Next, Laemmli sample buffer was added to 2 µL of each spinal fluid, and the mixture was heated and then subjected to SDS/PAGE using a 5 to 20%-gradient polyacrylamide gel. Electrophoresis was conducted at a constant current of 40 mA for 55 minutes. The isolated proteins of each sample were electrically transferred to a PVDF membrane at a constant current of 260 mA for 50 minutes by a blotting method known in the art. After the transfer, the membrane was blocked with PBS containing 1% BSA for 1 hour or longer. Subsequently, available antibodies (e.g., goat anti-human α2-macroglobulin antibody, ICN Biomedicals Inc. (Cappel), Cat. No. 55113; Abcam plc., Cat. No. ab84176; Santa Cruz Biotechnology, Inc., Cat. No. sc-8514; and Dako Japan Inc., Cat. No. Q0102)) against the spinal fluid glycoproteins set forth in Table 1 were each diluted with PBS containing 1% BSA, added thereto at final concentrations of 1 to 2 µg/mL, and reacted for 1 hour. The membrane was washed three times each for 15 minutes with a PBS washing solution containing 0.1% Tween 20. Then, the membrane was reacted for 1 hour with 1 µg/mL secondary antibody (donkey Anti-goat IgG Anti body-Horseradish Peroxidase, Santa Cruz Biotechnology, Inc., Cat. No. sc-2020) diluted 1:1000 with PBS containing 1% BSA. Again, the membrane was washed three times each for 15 minutes with the washing solution. The band of each spinal fluid glycoprotein was detected using a chemiluminescent substrate (Pierce SuperSignal West Dora Extended Duration Substrate) and Lumino Image Analyzer (LAS-1000 plus; Fujifilm Corp.).

(Results)

Figure 8:
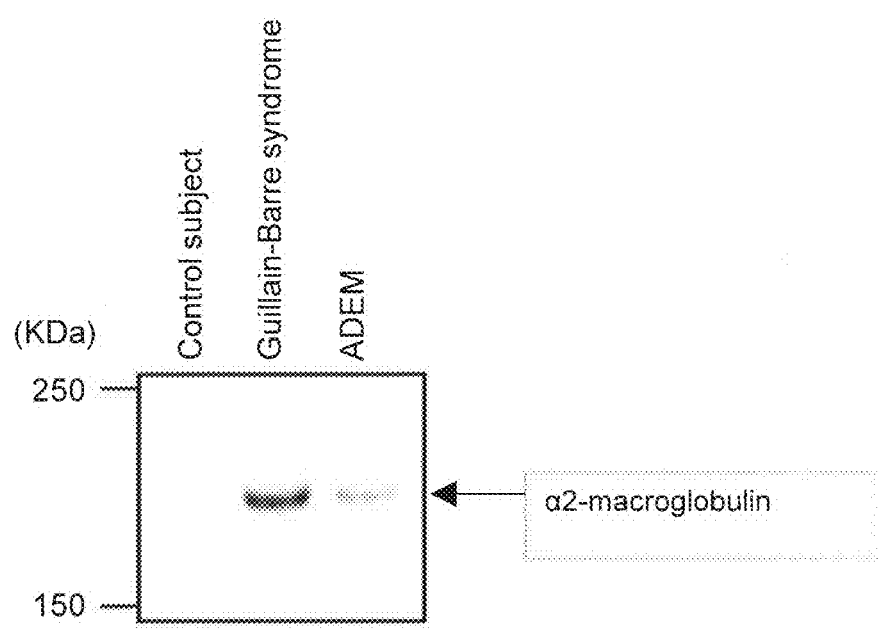
FIG. 8 is a diagram showing results of Western blotting by which α2-macroglobulin was detected from the respective spinal fluids of an acute disseminated encephalomyelitis (ADEM)-affected individual, a Guillain-Barre syndrome-affected individual, and a control subject (ADEM-unaffected/Guillain-Barre syndrome-unaffected individual) using an anti-α2-macroglobulin antibody.

The results are shown in FIG. 8. The results of examining the spinal fluid glycoproteins set forth in Table 1, for which antibodies were available, demonstrated that α2-macroglobulin obviously differs in expression level between ADEM or Guillain-Barre syndrome and the control subject. FIG. 8 shows the results of detecting α2-macroglobulin in each spinal fluid sample. The α2-macroglobulin exhibited an increased level in ADEM compared with the control subject. By contrast, as shown in Example 3, the α2-macroglobulin is hardly detected in MS. Thus, the α2-macroglobulin was shown to be an effective index marker for central nervous system disease for distinguishing ADEM from MS.

The α2-macroglobulin also exhibited an increased level in Guillain-Barre syndrome, demonstrating that the disease can be distinguished from multiple neuritis whose lesions are localized to peripheral nerves. Similar results were also obtained even using the anti-human α2-macroglobulin antibodies of other companies.

The results described above demonstrated that α2-macroglobulin can serve as a useful diagnostic marker capable of distinguishing ADEM from MS or Guillain-Barre syndrome from multiple neuritis.

(2) Search for Index Marker for Central Nervous System Disease for Distinguishing Status Epilepticus, Encephalopathy, and Viral Meningitis The "febrile convulsion" often found in children is convulsion that occurs in association with fever of 38 to 39° C. or higher. Convulsive seizure stops within 5 minutes, and the convulsion heals naturally without leaving neurological sequela. On the other hand, the "status epilepticus" is usually treated with an anticonvulsant agent because its seizure continues for 30 minutes or longer and may leave sequela when continuing for a time exceeding 90 minutes. Since convulsive seizure that continues for a time exceeding 30 minutes with fever may be responsible for status epilepticus as well as central nervous system infections such as meningitis, encephalitis, and encephalopathy, spinal fluid tests are required.

The "meningitis" includes bacterial meningitis and viral meningitis, both of which can be diagnosed by spinal fluid tests. For example, bacterial meningitis can be diagnosed on the basis of increase in neutrophil in spinal fluid, decrease in glucose concentration, etc., while viral meningitis can be diagnosed on the basis of increase in mononuclear cell. In addition, a standard treatment method has already been established for each meningitis.

The "encephalopathy" is a disease that occurs secondary to bacterial or viral infection. Although much remains unknown about its pathological conditions, this disease is allegedly based on the abnormal energy or electrolyte metabolism of the brain. The encephalopathy is a grave disease accompanied by brain swelling, disturbance of consciousness, convulsion, and fever. For example, the death rate of influenza encephalopathy reaches 50 to 60%.

A method for definitely distinguishing relatively mild status epilepticus, which is cured by the administration of an anticonvulsant agent, from encephalopathy, etc., has been unknown so far. Hence, the encephalopathy cannot be diagnosed at the first medical examination (during hospitalization) and is generally diagnosed at a later date by observing the course of its symptom or response to treatment.

Thus, the spinal fluid glycoproteins of Table 1 as index marker candidates for central nervous system disease identified in Example 2 were searched for an index marker for central nervous system disease capable of distinguishing encephalopathy from status epilepticus.

(Methodology)

Basic procedures are the same as in the paragraph (1). Spinal fluids were collected from a status epilepticus patient, an encephalopathy patient, and a viral meningitis patient. In this context, the encephalopathy patient was definitely diagnosed by follow-up after hospitalization. Samples were collected from the same encephalopathy patient at the first medical examination during hospitalization and after treatment (7 days later).

(Results)

Figure 9:
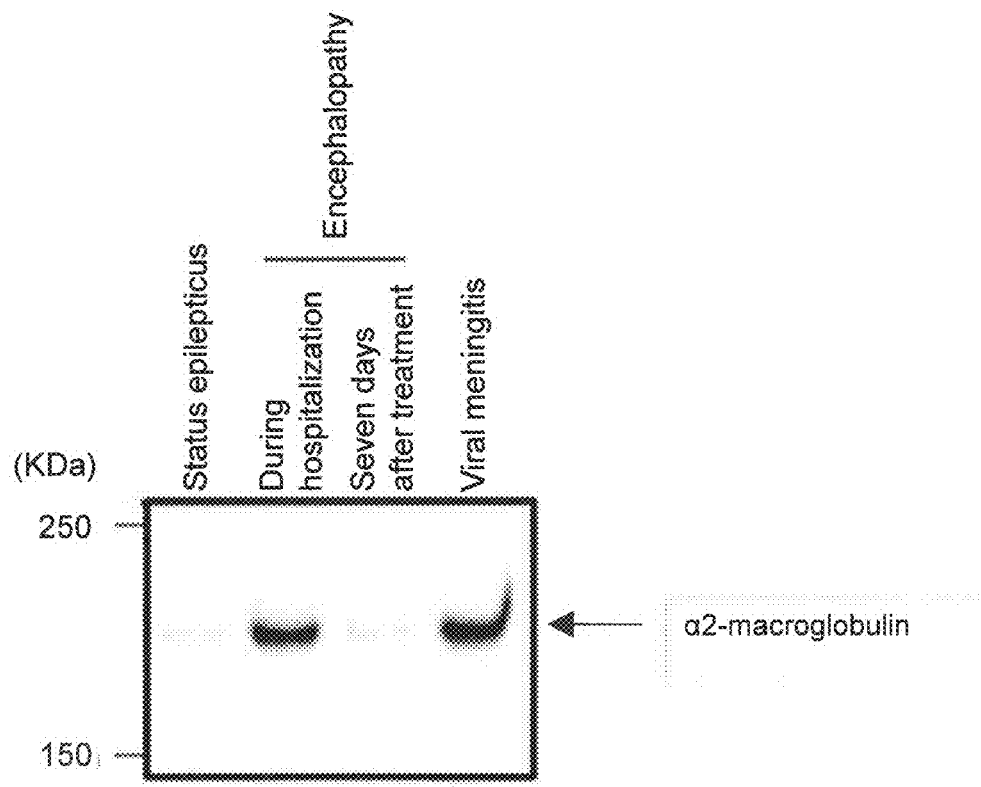
FIG. 9 is a diagram showing results of Western blotting by which α2-macroglobulin was detected from the respective spinal fluids of a status epilepticus-affected individual, an encephalopathy-affected individual (during hospitalization and 7 days after treatment), and a viral meningitis-affected individual using an anti-α2-macroglobulin antibody.

The results are shown in FIG. 9. The results of examining the spinal fluid glycoproteins set forth in Table 1, for which antibodies were available, demonstrated that α2-macroglobulin obviously differs in expression level between the status epilepticus patient and the encephalopathy patient. FIG. 9 shows the results of detecting α2-macroglobulin in each spinal fluid sample. The α2-macroglobulin was found only in a trace amount in the spinal fluid of the status epilepticus patient but exhibited a significantly increased level in the hospitalized encephalopathy patient, demonstrating that these diseases can be distinguished therebetween using α2-macroglobulin. As is evident from the diagram, the amount of α2-macroglobulin in the spinal fluid decreased and reached a normal level seven days after the treatment of encephalopathy. As in encephalopathy, α2-macroglobulin also exhibited an increased level in the spinal fluid of the viral meningitis patient. As mentioned above, viral meningitis can be diagnosed on the basis of increase in mononuclear cell, though encephalopathy and viral meningitis exhibit similar symptoms (convulsion). Thus, the diseases can be distinguished therebetween by a method other than use of α2-macroglobulin. Thus, the same behavior of α2-macroglobulin between the diseases does not matter.

Encephalopathy is treated by use of a strong formulation such as a steroid drug. Use of α2-macroglobulin as an index marker for the central nervous system disease, i.e., encephalopathy, permits determination of the timing of termination of the steroid drug treatment and can reduce adverse reaction caused by the excessive administration of the drug.

The results described above demonstrated that α2-macroglobulin can serve as an index marker for central nervous system disease capable of distinguishing encephalopathy patients from status epilepticus patients and encephalopathy patients.

Example 5

Search for Spinal Fluid Glycoprotein Serving as Alzheimer's Disease Marker.

Alzheimer's disease (AD) in patients is often found in so-called "forgetfulness" out-patient clinics. Dementia is classified according to its degree into 3 groups: normal aging, mild cognitive impairment, and AD. A patient whose brain atrophy has been confirmed by a morphological test (MRI or CT) is definitely diagnosed as an AD group. Unfortunately, such definite diagnosis at the end of the disease cannot be expected to lead to its cure because the majority of neural cells have already died. Now that therapeutic drugs for Alzheimer's disease are under clinical trials, a biomarker that permits early diagnosis has been demanded. In order to discover such a marker, a substance that exhibits a difference between the Alzheimer's disease group and the normal aging group is searched for by a primary screening method. Then, this marker is analyzed for whether or not to serve as an early diagnosis marker by the examination of its time-dependent change from normal aging through mild dementia to advanced Alzheimer's disease using the samples of patients. In this Example, prostaglandin D2 synthase (PGD2S) was identified as a spinal fluid glycoprotein that exhibited a difference between the Alzheimer's disease group and the normal aging group.

(Methodology)

PGD2S is present at a relatively large content in spinal fluid and as such, was analyzed directly by Western blotting without enrichment operation. The antibody used was an anti-human PGD2S antibody (Thermo Fisher Scientific Inc., Cat. No. PA1-46023) (1 μg/ml) and examined as to 2 individuals per group.

(Results)

Figure 10:
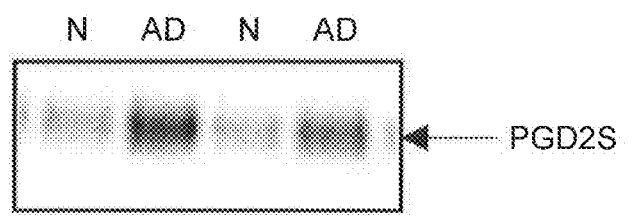
FIG. 10 shows results of detecting and quantifying prostaglandin-H2 D-isomerase (prostaglandin D2 synthase: PGD2S) in Alzheimer's disease (AD) and control spinal fluid (N) using an anti-PGD2S antibody.
Figure 11:
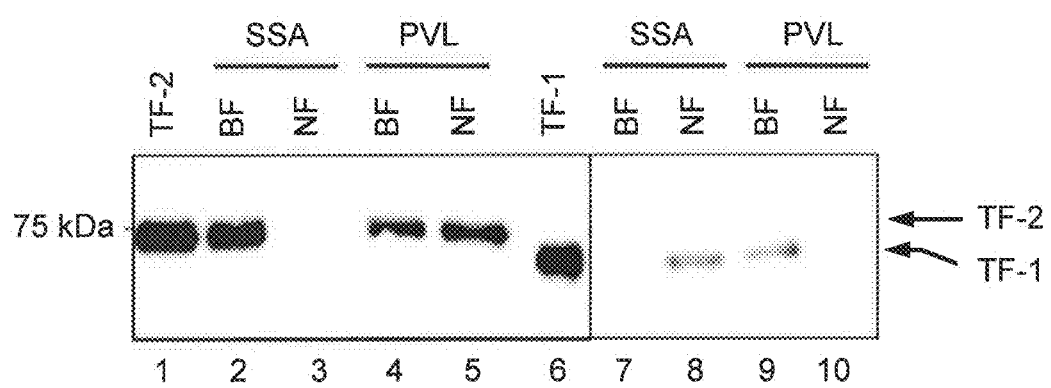
FIG. 11 shows results of Western blotting by which TF-1 or TF-2 contained in as binding fraction (BF) and a non-binding fraction (NF) of each lectin column was detected using an anti-transferrin antibody.

The results are shown in FIG. 10. The content of PGD2S was shown to increase in the Alzheimer's disease patients compared with the normal aging group. Quantitative analysis demonstrated that this increase was significant.

All publications, patents, and patent applications cited herein are incorporated herein by reference in their entirety.

We claim:

1. A method for distinguishing encephalopathy and viral meningitis from status epilepticus in a test subject suspected to have encephalopathy, viral meningitis or status epilepticus, the method comprising:
(1) binding a terminal N-acetylglucosamine-containing glycoprotein present in a spinal fluid sample obtained from the test subject to an N-acetylglucosamine-binding substance and isolating a formed complex;
(2) dissociating the complex and eluting the terminal N-acetylglucosamine-containing glycoprotein, and removing terminal sialic acid-containing glycoprotein from the spinal fluid sample using a sialic acid-binding substance, to produce a test sample that is enriched in terminal N-acetylglucosamine-containing glycoproteins;
(3) detecting the expression level of α2-macroglobulin in the test sample;
(4) comparing the expression level of the α2-macroglobulin in the test sample to the expression level of α2-macroglobulin in a control sample of spinal fluid from a control subject afflicted with status epilepticus; and
(5) determining whether the test subject has status epilepticus or one of encephalopathy and viral meningitis on the basis of the comparing;
wherein:
a higher level of expression of α2-macroglobulin in the test sample from the third test subject relative to the control sample from the control subject afflicted with status epilepticus indicates that the test subject is afflicted with encephalopathy or viral meningitis, and an equal level of expression in the test sample from the third test subject relative to the control sample from the control subject afflicted with status epilepticus indicates that the test subject is afflicted with status epilepticus, wherein the α2-macroglobulin has sugar chains which comprise N-acetylglucosamine residues but do not comprise α2,6 sialic acid residues at non-reducing termini of the sugar chains.

2. The method of claim 1, further comprising, prior to the removing terminal sialic acid-containing glycoprotein from the spinal fluid sample, a step of removing albumin from the spinal fluid using an albumin-binding substance.

3. The method of claim 1, wherein the sialic acid-binding substance is an anti-sialic acid antibody or an antigen binding fragment thereof, or a sialic acid-binding lectin.

4. The method of claim 1, wherein the sialic acid is α2,6 sialic acid.

5. The method of claim 4, wherein the α2,6 sialic acid-binding lectin is selected from the group consisting of SSA lectin, SNA lectin, and TJA-I lectin.

6. The method of claim 1, wherein the N-acetylglucosamine-binding substance is an anti-N-acetylglucosamine antibody or an antigen binding fragment thereof, or an N-acetylglucosamine-binding lectin.

7. The method of claim 6, wherein the N-acetylglucosamine-binding lectin is PVL lectin or WGA lectin.

8. The method of claim 2, wherein the albumin-binding substance is Blue Sepharose, or an anti-albumin antibody or an antigen binding fragment thereof.

9. The method of claim 1, wherein the α2-macroglobulin consists of the amino acid sequence of SEQ ID NO: 1.

* * * * *

SEQUENCE LISTING

<160> NUMBER OF SEQ ID NOS: 1

<210> SEQ ID NO 1
<211> LENGTH: 1474
<212> TYPE: PRT
<213> ORGANISM: Homo sapiens

<400> SEQUENCE: 1

| | | | | | | | | | | | | | | | |
|---|---|---|---|---|---|---|---|---|---|---|---|---|---|---|---|
| Met | Gly | Lys | Asn | Lys | Leu | Leu | His | Pro | Ser | Leu | Val | Leu | Leu | Leu | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Val | Leu | Leu | Pro | Thr | Asp | Ala | Ser | Val | Ser | Gly | Lys | Pro | Gln | Tyr | Met |
| | | | 20 | | | | | 25 | | | | | 30 | | |

| | | | | | | | | | | | | | | | |
|---|---|---|---|---|---|---|---|---|---|---|---|---|---|---|---|
| Val | Leu | Val | Pro | Ser | Leu | Leu | His | Thr | Glu | Thr | Thr | Glu | Lys | Gly | Cys |
| | | | | 35 | | | | | 40 | | | | | 45 | |

| | | | | | | | | | | | | | | | |
|---|---|---|---|---|---|---|---|---|---|---|---|---|---|---|---|
| Val | Leu | Leu | Ser | Tyr | Leu | Asn | Glu | Thr | Val | Thr | Val | Ser | Ala | Ser | Leu |
| | | | 50 | | | | | 55 | | | | | 60 | | |

| | | | | | | | | | | | | | | | |
|---|---|---|---|---|---|---|---|---|---|---|---|---|---|---|---|
| Glu | Ser | Val | Arg | Gly | Asn | Arg | Ser | Leu | Phe | Thr | Asp | Leu | Glu | Ala | Glu |
| 65 | | | | | 70 | | | | | 75 | | | | | 80 |

| | | | | | | | | | | | | | | | |
|---|---|---|---|---|---|---|---|---|---|---|---|---|---|---|---|
| Asn | Asp | Val | Leu | His | Cys | Val | Ala | Phe | Ala | Val | Pro | Lys | Ser | Ser | Ser |
| | | | | 85 | | | | | 90 | | | | | 95 | |

| | | | | | | | | | | | | | | | |
|---|---|---|---|---|---|---|---|---|---|---|---|---|---|---|---|
| Asn | Glu | Glu | Val | Met | Phe | Leu | Thr | Val | Gln | Val | Lys | Gly | Pro | Thr | Gln |
| | | | | 100 | | | | | 105 | | | | | 110 | |

| | | | | | | | | | | | | | | | |
|---|---|---|---|---|---|---|---|---|---|---|---|---|---|---|---|
| Glu | Phe | Lys | Lys | Arg | Thr | Thr | Val | Met | Val | Lys | Asn | Glu | Asp | Ser | Leu |
| | | | 115 | | | | | 120 | | | | | 125 | | |

| | | | | | | | | | | | | | | | |
|---|---|---|---|---|---|---|---|---|---|---|---|---|---|---|---|
| Val | Phe | Val | Gln | Thr | Asp | Lys | Ser | Ile | Tyr | Lys | Pro | Gly | Gln | Thr | Val |
| | | | 130 | | | | | 135 | | | | | 140 | | |

| | | | | | | | | | | | | | | | |
|---|---|---|---|---|---|---|---|---|---|---|---|---|---|---|---|
| Lys | Phe | Arg | Val | Val | Ser | Met | Asp | Glu | Asn | Phe | His | Pro | Leu | Asn | Glu |
| 145 | | | | | 150 | | | | | 155 | | | | | 160 |

| | | | | | | | | | | | | | | | |
|---|---|---|---|---|---|---|---|---|---|---|---|---|---|---|---|
| Leu | Ile | Pro | Leu | Val | Tyr | Ile | Gln | Asp | Pro | Lys | Gly | Asn | Arg | Ile | Ala |
| | | | | 165 | | | | | 170 | | | | | 175 | |

| | | | | | | | | | | | | | | | |
|---|---|---|---|---|---|---|---|---|---|---|---|---|---|---|---|
| Gln | Trp | Gln | Ser | Phe | Gln | Leu | Glu | Gly | Gly | Leu | Lys | Gln | Phe | Ser | Phe |
| | | | 180 | | | | | 185 | | | | | 190 | | |

| | | | | | | | | | | | | | | | |
|---|---|---|---|---|---|---|---|---|---|---|---|---|---|---|---|
| Pro | Leu | Ser | Ser | Glu | Pro | Phe | Gln | Gly | Ser | Tyr | Lys | Val | Val | Val | Gln |
| | | | 195 | | | | | 200 | | | | | 205 | | |

| | | | | | | | | | | | | | | | |
|---|---|---|---|---|---|---|---|---|---|---|---|---|---|---|---|
| Lys | Lys | Ser | Gly | Gly | Arg | Thr | Glu | His | Pro | Phe | Thr | Val | Glu | Glu | Phe |
| | | | 210 | | | | | 215 | | | | | 220 | | |

| | | | | | | | | | | | | | | | |
|---|---|---|---|---|---|---|---|---|---|---|---|---|---|---|---|
| Val | Leu | Pro | Lys | Phe | Glu | Val | Gln | Val | Thr | Val | Pro | Lys | Ile | Ile | Thr |
| 225 | | | | | 230 | | | | | 235 | | | | | 240 |

| | | | | | | | | | | | | | | | |
|---|---|---|---|---|---|---|---|---|---|---|---|---|---|---|---|
| Ile | Leu | Glu | Glu | Glu | Met | Asn | Val | Ser | Val | Cys | Gly | Leu | Tyr | Thr | Tyr |
| | | | | 245 | | | | | 250 | | | | | 255 | |

| | | | | | | | | | | | | | | | |
|---|---|---|---|---|---|---|---|---|---|---|---|---|---|---|---|
| Gly | Lys | Pro | Val | Pro | Gly | His | Val | Thr | Val | Ser | Ile | Cys | Arg | Lys | Tyr |
| | | | | 260 | | | | | 265 | | | | | 270 | |

| | | | | | | | | | | | | | | | |
|---|---|---|---|---|---|---|---|---|---|---|---|---|---|---|---|
| Ser | Asp | Ala | Ser | Asp | Cys | His | Gly | Glu | Asp | Ser | Gln | Ala | Phe | Cys | Glu |
| | | | 275 | | | | | 280 | | | | | 285 | | |

| | | | | | | | | | | | | | | | |
|---|---|---|---|---|---|---|---|---|---|---|---|---|---|---|---|
| Lys | Phe | Ser | Gly | Gln | Leu | Asn | Ser | His | Gly | Cys | Phe | Tyr | Gln | Gln | Val |
| | | | 290 | | | | | 295 | | | | | 300 | | |

| | | | | | | | | | | | | | | | |
|---|---|---|---|---|---|---|---|---|---|---|---|---|---|---|---|
| Lys | Thr | Lys | Val | Phe | Gln | Leu | Lys | Arg | Lys | Glu | Tyr | Glu | Met | Lys | Leu |
| 305 | | | | | 310 | | | | | 315 | | | | | 320 |

| | | | | | | | | | | | | | | | |
|---|---|---|---|---|---|---|---|---|---|---|---|---|---|---|---|
| His | Thr | Glu | Ala | Gln | Ile | Gln | Glu | Glu | Gly | Thr | Val | Val | Glu | Leu | Thr |
| | | | | 325 | | | | | 330 | | | | | 335 | |

| | | | | | | | | | | | | | | | |
|---|---|---|---|---|---|---|---|---|---|---|---|---|---|---|---|
| Gly | Arg | Gln | Ser | Ser | Glu | Ile | Thr | Arg | Thr | Ile | Thr | Lys | Leu | Ser | Phe |
| | | | 340 | | | | | 345 | | | | | 350 | | |

| | | | | | | | | | | | | | | | |
|---|---|---|---|---|---|---|---|---|---|---|---|---|---|---|---|
| Val | Lys | Val | Asp | Ser | His | Phe | Arg | Gln | Gly | Ile | Pro | Phe | Phe | Gly | Gln |
| | | | 355 | | | | | 360 | | | | | 365 | | |

-continued

```
Val Arg Leu Val Asp Gly Lys Gly Val Pro Ile Pro Asn Lys Val Ile
    370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu His Glu Ala His Thr Ala
                435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
                500                 505                 510

Leu Leu Val Lys Gln Glu Asp Met Lys Gly His Phe Ser Ile Ser Ile
                515                 520                 525

Pro Val Lys Ser Asp Ile Ala Pro Val Ala Arg Leu Leu Ile Tyr Ala
                530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
        610                 615                 620

Lys Asp Leu Thr Gly Phe Pro Gly Pro Leu Asn Asp Gln Asp Asn Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
            675                 680                 685

Cys Pro Gln Leu Gln Gln Tyr Glu Met His Gly Pro Glu Gly Leu Arg
        690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
                740                 745                 750

Glu Val Gly Val Thr Val Pro Asp Thr Ile Thr Glu Trp Lys Ala Gly
                755                 760                 765

Ala Phe Cys Leu Ser Glu Asp Ala Gly Leu Gly Ile Ser Ser Thr Ala
770                 775                 780

Ser Leu Arg Ala Phe Gln Pro Phe Phe Val Glu Leu Thr Met Pro Tyr
```

-continued

```
            785                 790                 795                 800
        Ser Val Ile Arg Gly Glu Ala Phe Thr Leu Lys Ala Thr Val Leu Asn
                        805                 810                 815

Tyr Leu Pro Lys Cys Ile Arg Val Ser Val Gln Leu Glu Ala Ser Pro
                        820                 825                 830

Ala Phe Leu Ala Val Pro Val Glu Lys Glu Gln Ala Pro His Cys Ile
                        835                 840                 845

Cys Ala Asn Gly Arg Gln Thr Val Ser Trp Ala Val Thr Pro Lys Ser
                        850                 855                 860

Leu Gly Asn Val Asn Phe Thr Val Ser Ala Glu Ala Leu Glu Ser Gln
        865                 870                 875                 880

Glu Leu Cys Gly Thr Glu Val Pro Ser Val Pro Glu His Gly Arg Lys
                        885                 890                 895

Asp Thr Val Ile Lys Pro Leu Leu Val Glu Pro Glu Gly Leu Glu Lys
                        900                 905                 910

Glu Thr Thr Phe Asn Ser Leu Leu Cys Pro Ser Gly Gly Glu Val Ser
                        915                 920                 925

Glu Glu Leu Ser Leu Lys Leu Pro Pro Asn Val Val Glu Glu Ser Ala
        930                 935                 940

Arg Ala Ser Val Ser Val Leu Gly Asp Ile Leu Gly Ser Ala Met Gln
        945                 950                 955                 960

Asn Thr Gln Asn Leu Leu Gln Met Pro Tyr Gly Cys Gly Glu Gln Asn
                        965                 970                 975

Met Val Leu Phe Ala Pro Asn Ile Tyr Val Leu Asp Tyr Leu Asn Glu
                        980                 985                 990

Thr Gln Gln Leu Thr Pro Glu Ile Lys Ser Lys Ala Ile Gly Tyr Leu
                        995                 1000                1005

Asn Thr Gly Tyr Gln Arg Gln Leu Asn Tyr Lys His Tyr Asp Gly
                    1010                1015                1020

Ser Tyr Ser Thr Phe Gly Glu Arg Tyr Gly Arg Asn Gln Gly Asn
                    1025                1030                1035

Thr Trp Leu Thr Ala Phe Val Leu Lys Thr Phe Ala Gln Ala Arg
                    1040                1045                1050

Ala Tyr Ile Phe Ile Asp Glu Ala His Ile Thr Gln Ala Leu Ile
                    1055                1060                1065

Trp Leu Ser Gln Arg Gln Lys Asp Asn Gly Cys Phe Arg Ser Ser
                    1070                1075                1080

Gly Ser Leu Leu Asn Asn Ala Ile Lys Gly Gly Val Glu Asp Glu
                    1085                1090                1095

Val Thr Leu Ser Ala Tyr Ile Thr Ile Ala Leu Leu Glu Ile Pro
                    1100                1105                1110

Leu Thr Val Thr His Pro Val Val Arg Asn Ala Leu Phe Cys Leu
                    1115                1120                1125

Glu Ser Ala Trp Lys Thr Ala Gln Glu Gly Asp His Gly Ser His
                    1130                1135                1140

Val Tyr Thr Lys Ala Leu Leu Ala Tyr Ala Phe Ala Leu Ala Gly
                    1145                1150                1155

Asn Gln Asp Lys Arg Lys Glu Val Leu Lys Ser Leu Asn Glu Glu
                    1160                1165                1170

Ala Val Lys Lys Asp Asn Ser Val His Trp Glu Arg Pro Gln Lys
                    1175                1180                1185

Pro Lys Ala Pro Val Gly His Phe Tyr Glu Pro Gln Ala Pro Ser
                    1190                1195                1200
```

```
Ala Glu Val Glu Met Thr Ser Tyr Val Leu Leu Ala Tyr Leu Thr
    1205            1210                1215

Ala Gln Pro Ala Pro Thr Ser Glu Asp Leu Thr Ser Ala Thr Asn
    1220            1225                1230

Ile Val Lys Trp Ile Thr Lys Gln Gln Asn Ala Gln Gly Gly Phe
    1235            1240                1245

Ser Ser Thr Gln Asp Thr Val Val Ala Leu His Ala Leu Ser Lys
    1250            1255                1260

Tyr Gly Ala Ala Thr Phe Thr Arg Thr Gly Lys Ala Ala Gln Val
    1265            1270                1275

Thr Ile Gln Ser Ser Gly Thr Phe Ser Ser Lys Phe Gln Val Asp
    1280            1285                1290

Asn Asn Asn Arg Leu Leu Leu Gln Gln Val Ser Leu Pro Glu Leu
    1295            1300                1305

Pro Gly Glu Tyr Ser Met Lys Val Thr Gly Glu Gly Cys Val Tyr
    1310            1315                1320

Leu Gln Thr Ser Leu Lys Tyr Asn Ile Leu Pro Glu Lys Glu Glu
    1325            1330                1335

Phe Pro Phe Ala Leu Gly Val Gln Thr Leu Pro Gln Thr Cys Asp
    1340            1345                1350

Glu Pro Lys Ala His Thr Ser Phe Gln Ile Ser Leu Ser Val Ser
    1355            1360                1365

Tyr Thr Gly Ser Arg Ser Ala Ser Asn Met Ala Ile Val Asp Val
    1370            1375                1380

Lys Met Val Ser Gly Phe Ile Pro Leu Lys Pro Thr Val Lys Met
    1385            1390                1395

Leu Glu Arg Ser Asn His Val Ser Arg Thr Glu Val Ser Ser Asn
    1400            1405                1410

His Val Leu Ile Tyr Leu Asp Lys Val Ser Asn Gln Thr Leu Ser
    1415            1420                1425

Leu Phe Phe Thr Val Leu Gln Asp Val Pro Val Arg Asp Leu Lys
    1430            1435                1440

Pro Ala Ile Val Lys Val Tyr Asp Tyr Tyr Glu Thr Asp Glu Phe
    1445            1450                1455

Ala Ile Ala Glu Tyr Asn Ala Pro Cys Ser Lys Asp Leu Gly Asn
    1460            1465                1470

Ala
```